(12) United States Patent
Oeltjen

(10) Patent No.: US 9,128,069 B2
(45) Date of Patent: Sep. 8, 2015

(54) ANALYSIS SYSTEM AND COMPUTER IMPLEMENTED METHOD FOR ANALYZING BIOLOGICAL SAMPLES

(75) Inventor: Lars Oeltjen, Zug (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1268 days.

(21) Appl. No.: 12/976,071

(22) Filed: Dec. 22, 2010

(65) Prior Publication Data

US 2012/0004853 A1  Jan. 5, 2012

(30) Foreign Application Priority Data

Dec. 23, 2009 (EP) .................................... 09180643

(51) Int. Cl.
*G01N 33/48* (2006.01)
*G01N 35/00* (2006.01)
*G06F 19/28* (2011.01)

(52) U.S. Cl.
CPC ...... *G01N 35/00663* (2013.01); *G01N 35/0092* (2013.01); *G01N 2035/00752* (2013.01); *G01N 2035/00801* (2013.01); *G01N 2035/00831* (2013.01); *G01N 2035/00851* (2013.01); *G06F 19/28* (2013.01)

(58) Field of Classification Search
CPC ...................................................... G06F 19/28
USPC .......................................................... 702/19
See application file for complete search history.

(56) References Cited

U.S. PATENT DOCUMENTS

| 5,314,825 | A | 5/1994 | Weyrauch et al. |
| 5,366,896 | A | 11/1994 | Margrey et al. |
| 5,817,519 | A * | 10/1998 | Zelmanovic et al. ........... 436/63 |
| 2004/0175840 | A1 | 9/2004 | Devlin, Sr. et al. |
| 2005/0019223 | A1 * | 1/2005 | Platt et al. ..................... 422/100 |
| 2009/0053111 | A1 | 2/2009 | Francis |
| 2009/0142231 | A1 | 6/2009 | Shibuya et al. |
| 2010/0001876 | A1 | 1/2010 | Sasaki |

FOREIGN PATENT DOCUMENTS

| DE | 20121738 U1 | 9/2003 |
| EP | 0 990 905 A1 | 4/2000 |
| EP | 1 770 399 A1 | 4/2007 |
| JP | 2004514910 A | 5/2004 |
| JP | 2005106667 A | 4/2005 |
| WO | 2005/093641 A1 | 10/2005 |
| WO | 2008/126589 A1 | 10/2008 |

* cited by examiner

*Primary Examiner* — Jerry Lin
(74) *Attorney, Agent, or Firm* — Dinsmore & Shohl LLP

(57) ABSTRACT

Analysis system and computer implemented method for analyzing biological samples are disclosed. The system has at least one analyzer for performing an analysis and a decision unit being operable to determine in response to the receipt of the analysis request whether results obtained from performing the analysis on the sample indicated in the analysis request are valid. This determination is executed by retrieving the meta information assigned to the sample and by applying the at least one condition on the meta information and wherein the at least one applied condition has at least a condition on whether the sample allows a valid analysis on the sample, and wherein the decision unit returns the decision that the analysis exercised on the indicated sample will return a valid result in case the conditions of the condition set are met by the sample.

13 Claims, 6 Drawing Sheets

ANALYSIS SYSTEM AND COMPUTER IMPLEMENTED METHOD FOR ANALYZING BIOLOGICAL SAMPLES

TECHNICAL FIELD

The present disclosure relates to an analysis system and computer implemented method for analyzing biological samples, such as body fluids.

BACKGROUND

The management of biological samples is a highly complex task due to the multitude of operational steps and the multitude of procedural and security aspects that have to be considered ahead of the execution of each working step. Currently, many of those working steps are executed manually, resulting in prolonged sample processing workflows and an increased risk of erroneous analysis results. The risk of an accidental contact of the lab personnel with the potentially infectious content of biological samples should also be mentioned in this context.

Biological samples, such as tissues, blood, saliva or urine samples are routinely taken from patients by medical personnel in hospitals or in a doctor's practice. They are used for various analyses. Analyses are laboratory procedures determining, for example, the glucose, Fe2+, haematocrite, kreatinine or leukocyte level of the blood or other types of samples. The concentration values obtained from those analyses are important aids in the diagnosis of diseases and are important indicators of the state of health of a patient.

Usually, a sample taken from the patient or laboratory animal provides enough material for multiple analyses. This ensures that a patient does not have to appear a second time and provide an additional blood sample in case an analysis fails or has for other reasons to be repeated, e.g. in case the doctor considers additional diagnostic tests as necessary. For those reasons, a biological sample is usually aliquoted and stored under conditions extending the stability and storage life of the biological sample as long as possible. The process of sample aliquotation yields small sample volumes which can be directly used for analysis.

The storage conditions prolonging the storage life of biological samples usually comprise a low temperature level, e.g. some degrees centigrade above freezing temperature in a refrigerator or even lower temperatures as provided by a freezer.

If a particular analysis has to be executed on a sample, e.g. an analysis determining the glucose level of a blood sample of a patient, the blood sample or an aliquot of the blood sample of that patient has to be taken from the storage device to the biomedical analyzer in which the analysis shall be exercised. The results generated by the analysis are returned to the medical personnel and are used, for example, to determine the status of health of a patient or to monitor the effects of a medical treatment or medication on the patient.

Currently, many of the tasks mentioned beforehand have to be executed manually. The blood sample is aliquoted by a lab professional into smaller samples and manually labeled with the date and time of sample preparation and with an identifier enabling the association of the sample with a particular patient, e.g. a bar code label or a hand written patient number and sampling time written onto the sample. The samples are transferred manually to the storage device. In case an analysis is to be executed on an already stored sample to determine a particular analyte e.g. in the blood of a patient, the lab personnel has to identify the appropriate sample in the storage device manually, has to decap or otherwise pre-process the sample, and has to transfer it to the analyzer.

Multiple sources of errors exist according to said scenario: the lab personnel may have labeled the sample erroneously, may have taken a wrong sample belonging to a different patient for analysis out of the storage or may have used a sample for analysis although the storage duration of that sample was too long to guarantee valid analysis results. In addition, each interaction of a human with a biological sample can be considered as security risk as a sample may have been derived from a patient having an infectious disease.

The use of a sample being too old to apply a particular analysis can have fatal consequences: if the analysis results obtained are wrong due to the age of the sample, wrong analysis results may be obtained resulting in an inappropriate diagnosis or treatment of a patient. The lab personnel therefore has to guarantee somehow that the storage duration of the sample given the storage conditions still enable the retrieval of valid analysis results on that sample and, if not, that said sample is not used for analysis.

Currently, samples are therefore discarded after a predetermined period of time, e.g. one or two weeks, or according to the decision of each individual lab worker applying rules of thumb. The disposal of biological samples according to said rules shall ensure that all stored samples can be used for analysis and that the validity of the analysis result is not negatively affected by the age of the samples. This 'solution' is connected with several significant disadvantages: the maximum possible storage duration of a sample still allowing the retrieval of valid results by an analysis depends not only on the storage length and storage conditions but also on the sample type (blood, urine) and the kind of analysis to be performed (the type and property of the analyte to be characterized, e.g. the concentration of glucose, lactate or Troponin-T). The disposal of samples after a fixed period of storage time after which the samples are too old for a particular analysis therefore may lead to a disposal of samples which are still usable for some other kinds of analysis. This solution cannot be considered as optimal, as samples which could have been used for other types of analyses are disposed and more samples have to be taken from the patient as necessary. This results in increased costs, because the patient has to arrange an additional appointment at the hospital, where a new sample, e.g. a blood sample, is taken, because more waste is produced than necessary by disposing samples that could have still be usable for some analyses, and because the lab personnel has additional work with sampling, preprocessing and storing the new samples. The manual disposal of samples after a fixed period of time is very time consuming: in most biomedical laboratories, a multitude of samples is taken from patients, labeled and stored appropriately every day. In case the laboratory supervisor instructs the lab personnel to discards all samples being older than one week to ensure that older samples cannot be used for an analysis requiring a sample age of at the maximum 7 days, the lab personnel may check the age of all stored samples e.g. once a week every Friday. The problem arises that a sample having been taken from a patient on Monday in a particular week will not be disposed during the manual check of sample age executed on Friday of the same week, but will have expired on Monday the next week. As the next manual check of the sample age will be executed on Friday the next week, there is the danger that an analysis request submitted Tuesday, Wednesday or Thursday in the next week will be executed on an old sample resulting in a wrong analysis result. In order to guarantee that this scenario does not happen, the manual examination of the sample age has to be executed much more frequently than the maximum storage time of a sample, e.g. on a daily basis. Another solution is to manually check the sample age of each sample for every individual analysis request on a sample. Both described solutions are current methods in many biomedical laboratories, but both are highly time consuming and error prone.

In the context of biomedical research, an analysis is a technical procedure to characterize the parameter of a biological sample or of an analyte of the sample. The characterization of a parameter of a sample comprises, for example, the determination of the concentration of particular proteins, metabolites, ions or molecules of various sizes in biological samples derived from humans or laboratory animals. The gathered information can be used to evaluate e.g. the impact of the administration of drugs on the organism or on particular tissues. Further analyses may determine optical, electrochemical or other parameters of the samples or the analytes comprised in a sample.

Various analyzers are known for analyzing biological samples in-vitro providing the lab professionals with means to automate some of the above mentioned tasks. One such analyzer, for example, stores for each reagent used a predetermined period of time ranging from the opening of a reagent vessel to the deterioration of the reagent. A reagent is the substance used in an analysis to detect or otherwise characterize an analyte of a sample. The analyzer judges whether a calibration curve factor for a reagent set is applicable or not to another reagent set of the analyzer with the same production number based on the predetermined period of time from the reagent vessel unsealing to the expiration date of the reagent. Another such automatic analyzer is operable to change reagents during analysis without stopping the analysis in the event that a reagent shortage occurs during the analysis. A reagent is transferred from a reagent storage unit to a reagent changing mechanism. Then, the reagent changing mechanism is moved so that reagents are changed.

Such analyzers automate and improve some singular steps of the analysis process chain of a biological sample, e.g. the task of allocating a reagent required for an analysis, thereby taking into consideration the expiration date, the opening of the reagent vessel or the amount of reagent still available in the reagent lot of an analyzer. The prior art, however, does not address the fact that the stability of biological samples is often even more time critical than the expiration date of the reagent. While various buffers and detection reagents may have a storage life of month or even years, the storage life of biological samples is often considerably shorter. Depending on the biological sample and on the analysis to be performed on the sample, the time window within which an analysis can be performed on the sample is often measured in few days given optimal storage conditions.

Prior art systems are not capable of considering the impact of the storage life of a biological sample on the question if an analysis can still be applied on the sample. In particular, they do not address the problem that the maximum acceptable storage life for performing an analysis on a sample does not only depend on the storage time, but also on the type of analysis to be executed on the sample.

SUMMARY

In one embodiment, an analysis system for analyzing biological samples is disclosed. The system comprises at least one analyzer which performs an analysis, the analyzer operates to characterize a property of an analyte of a biological sample and to acquire at least one measurement value as a result of the characterization; a receiver which receives unique sample identifiers, each one of the unique sample identifiers identifying one of the biological samples; a set of program instructions which cause assigning meta information to each sample identifier, the meta information comprising at least a point in time information being indicative of the age of the sample, and storing each received identifier and its assigned sample meta information; a storage component which stores condition sets, each condition set corresponding to an analytical test and comprising at least one condition that has to be met by a sample to be usable for performing said analytical test by the analyzer, each said condition set comprising at least one condition for the age of the sample; an interface which receives an analysis request, the analysis request being at least indicative of one sample to be analyzed and at least one analytical test to be performed; a decision unit which operates to determine in response to the receipt of the analysis request whether results to be obtained from performing the analysis on the sample indicated in the analysis request will be valid, wherein this determination is executed by retrieving the meta information assigned to the sample and by applying the at least one condition on the meta information and wherein the at least one applied condition comprises at least a condition on whether the age of the sample allows a valid analysis on the sample, and wherein the decision unit returns the decision that the analysis to be exercised on the indicated sample will return a valid result in case the conditions of the condition set are met by the sample; and a controller which operates to initiate the analyzer to perform the analysis using the sample if it is determined that the sample is usable.

In another embodiment, a computer implemented method for analyzing biological samples by an analysis system is disclosed. The method may comprise receiving unique sample identifiers of the one or multiple biological samples loaded by a receiver of the analysis system; assigning meta information to each of the one or more biological samples; storing the meta information assigned to the unique sample identifier of the biological sample; receiving an analysis request being indicative of the biological sample to be analyzed and of an analytical test to be performed on the biological sample; determining, by a decision unit of the analysis system and in response to receiving the analysis request, whether the biological sample indicated in the analysis request is usable for performing the analysis by retrieving from a database the meta information stored in association with the unique sample identifier of the indicated biological sample, retrieving at least the condition set being associated with the requested analysis from a storage medium, checking, if the conditions of the retrieved condition set on the meta information of the indicated biological sample are met, wherein the conditions of the condition set have to be met by a biological sample to be usable for performing the requested analysis on the biological sample; and executing the requested analysis on the biological sample by an analyzer if according to the results of the previous step the indicated biological sample is usable for the requested analysis, wherein the meta information comprises at least a point in time information being indicative of the age of the biological sample and wherein the conditions comprise at least a condition on whether the age of the biological sample allows a valid analysis on the biological sample.

These and further features and advantages of these and other embodiments of the invention will appear more fully from the following description and the accompanying drawings.

BRIEF DESCRIPTION OF THE DRAWINGS

In the figures, like features are designated with like symbols, and in which.

Figure 1:
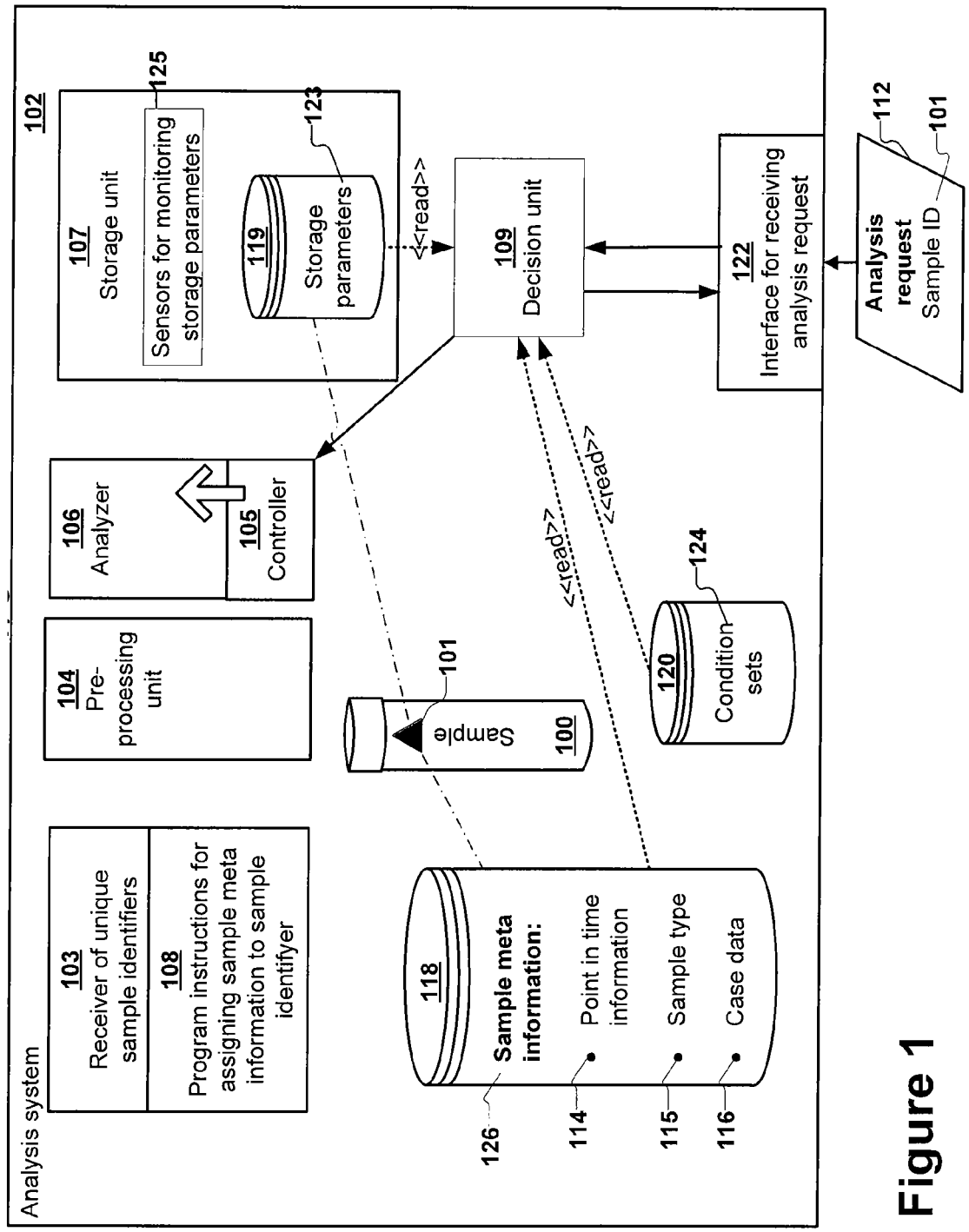
FIG. 1 is a block diagram of an embodiment of an analysis system of the invention.

LIST OF REFERENCE NUMERALS 100 sample
101 unique sample identifier
102 analysis system
103 receiver of unique sample identifiers
104 pre-processing unit
105 controller
106 analyzer
107 storage unit
108 set of program instructions
109 decision unit
110 step
111 step
112 analysis request
113 step
114 point in time information
115 data on sample type
116 case data
118 data storage
119 data storage
120 data storage
122 interface for receiving analysis request
123 storage parameters
124 condition sets
125 sensors for monitoring storage parameters
126 sample meta information
200-216 step
217 decision
218 step
300 step
301 device
302 device
303 message
305 transportation line
400 step
401 step
402 step
403 step
404 step
420 man machine interface
421 articulated arm
422 robotic arm
423 touch screen monitor
424 opening
425 capping station with feeder tank 426
426 feeder tank for tube caps
427 rack handler section
428 drawer
429 drawer
430 storage retrieval module
431 storage unit
432 disposal unit
433 refrigerator
501 IT infrastructure, e.g. middleware or LIS
502 computer or terminal
503 network
504 server
505 interface
506 data exchange decision unit—other components of analysis system
507 components of analysis system

DETAILED DESCRIPTION

Embodiments of the present invention are particularly advantageous, because they provide a user with means to automatically predict the usability of a sample for a particular analysis in dependence of the age of the sample in advance. Even more advantageous is the feature provided by further embodiments of the invention being operable to determine the usability of a sample for a particular analysis in dependence of the sample age and the actual storage conditions of the sample. The storage conditions of biological samples, e.g. the storage temperature, luminosity, humidity or other storage parameters, has an important influence on the applicability of a particular type of analysis on a sample. The storage conditions of samples are sometimes not as constant as they are assumed to be by the lab professionals. For example, if the door of a freezer or a refrigerator storing samples has been opened multiple times or several times for a prolonged time span, if the laboratory staff has forgotten to close a door of a freezer or refrigerator properly, or if the power supply of the device failed for some hours, the factual storage conditions may deviate significantly from the optimal storage conditions, potentially resulting in the usage of samples for analyses which should actually have been disposed. The storage conditions are according to said embodiments of the invention monitored automatically and used in addition to the age of the sample for the prediction if an analysis executed on a sample will yield valid results.

An additional problem solved by embodiments of the invention is the fact that the documentation of the storage conditions along the processing chain of a sample is fragmentary according to prior art technology. Even in case the cooling device constantly brings the samples stored therein to the correct temperature during the whole storage time of the sample, there is no guarantee that the sample was indeed stored constantly under said temperature. In case multiple analyses have to be executed on a sample, the lab personnel has to repeatedly transfer the sample from the cooling device to the workbench or the analyzer where the analysis is performed and to transfer the sample back to the storage after completion of the analysis. It is well known that in praxis there exist a multitude of situations in which a lab worker can be distracted from said task of transferring a sample to and from the storage, e.g. an urgent phone call, a laboratory procedure running in parallel and requiring immediate intervention by the lab personnel due to a process failure or the like. In such situations, a sample may be placed a prolonged time on the workbench without appropriate cooling. As this situation is usually not documented, another person may use said sample for analysis although it is not usable for analysis any more due to the interruption of the cold chain for a considerable period of time. The analysis results obtained from said sample may be invalid and lead to false diagnosis and decisions by medical professionals. Embodiments of the present invention document the whole processing chain of a sample beginning with loading the sample to the analysis unit, after which the samples are automatically transferred to an analyzer and a storage unit where the storage conditions of the sample is monitored automatically. According to further embodiments, the time of loading and unloading the sample to and from the storage unit is documented automatically, resulting in a complete documentation of the processing chain of each individual sample.

Further embodiments of the invention in addition check the type of a sample which also has an impact on the question if an analysis characterizing a particular analyte in a sample still yields valid results. Frequently analyzed types of biological samples are blood samples, serum samples or urine samples but a multitude of analyses and procedures exist based on other sample types, e.g. saliva or tissue samples.

In accordance with embodiments of the invention, an analysis system for analyzing biological samples is provided that comprises at least one analyzer. The analyzer is adapted to analyze a biological sample, such as a body fluid. Depending on the embodiment of the invention, the analyzer may be capable to execute only one particular kind of analysis or execute multiple different kinds of analyses on one or multiple different kinds of biological samples. The analysis comprises the characterization of an analyte of the sample or the characterization of a spectrometric, morphological or optical property of the sample such as opacity or fluorescence and the determination of electrophysiological or osmotic properties. In addition, the analysis may comprise the detection of an analyte, e.g. a protein, metabolite, ion or organic or inorganic molecule in the sample and the determination of the concentration or another feature of said analyte in the sample. The analyzer is operable to execute one particular or multiple analyses automatically, depending on the embodiment of the invention. The automated execution of an analysis may comprise the adding of one or multiple reactants necessary to detect or characterize the analyte or to reveal the optical or biochemical property of the sample to be detected. The adding of one or multiple reactants may result in a reaction of the reactant with the analyte resulting in the change of parameters which can be detected by the analyzer, e.g. a change in color, a change of opacity, or the like. Possible reactions comprise, but are not limited to, the creation or resolution of covalent chemical bonds, of hydrogen bridges, ion bonds or weak interactions.

According to a further embodiment of the invention, the analyzer measures a property of the sample and is capable of retrieving at least one measurement value for the examined property, the property being taken from the group consisting of biochemical, physical, optical, spectroscopic, osmotic, morphological or electric properties.

The analysis system in accordance with embodiments of the invention further comprises a receiver being operable to receive unique identifiers of a sample that is loaded into the analysis system. The unique identifier can be a bar code label on the tube, an RFID chip or any other label guaranteeing the unique identification and automatic recognition of that identifier. According to some embodiments of the invention, a sample can be uniquely identified by a combination of the unique rack identifier attached to the rack a sample is contained in combination with the position of the sample within this rack, e.g. a combination of values representing the lines and columns of the rack. The value combination 4/7 may, for example, indicate a sample being located on the fourth column in row 7.

According to a further embodiment of the invention, the unique sample identifier, e.g., a bar code or a RFID tag, on a sample is unique for the patient the sample was derived from, not for the sample. The unique sample identifier representing a sample on a particular position on a rack is in this embodiment built by a combination of a unique identifier for the patient or lab animal the sample was derived from according to the bar code information on a sample and a time information indicating the time the sample was loaded into the storage unit of the analysis system. A data value indicating the date and time of a particular event is in the following also referred to as 'timestamp'. Said embodiment requires that no two samples are loaded into the analysis system at the same time and that the receiver at the same time detects the position of the sample in the rack ensuring that the sample can be localized by its unique identifier composed from the patient specific bar code label and the timestamp.

The analysis system in accordance with embodiments of the invention further comprises a controller for the analyzer. The controller is capable to receive requests from other components of the analysis system, e.g. from a decision unit or data manager, to execute an analysis on a particular sample and to initiate the analysis by sending an initiation command to the analyzer. In addition, the controller in operation returns the analysis result retrieved from the analyzer to the system component from which the analysis request was received. In accordance with a further embodiment of the invention, the controller has a monitor coupled to it and/or it has an input unit coupled to it such that a user interaction with the controller of the analyzer is possible.

The analysis system in accordance with embodiments of the invention further comprises an interface for receiving analysis requests, the analysis request comprising at least information on the unique sample identifier of the sample which shall be analyzed. In case the analyzer of the analysis system is capable to execute multiple different analyses, the request is required to comprise in addition information on which kind of analysis is to be executed by the analyzer on the sample indicated in the request.

An 'analysis' is the study of the chemical composition and/or the characterization of various chemical, physical or optical properties of a biological sample or of the sample components. Typically, one particular substance, the analyte, is characterized during the analysis. The characterization of an analyte may comprise the determination of the concentration of the analyte, including the determination whether the analyte can be detected within the sample at all. The characterization may comprise the determination of geometric features, e.g. morphological properties of cells or tissues, the detection of organisms, e.g. pathogenic bacteria, protozoa or their traces left in the sample, optical and spectroscopic parameters, e.g. opacity, molecular biological and genetic features of a sample, e.g. the presence of a DNA or RNA sequence, the characterization of a particular protein or metabolite, and the determination of chemical features, e.g. the concentration of ions, organic and inorganic molecules. According to typical use case scenario of biomedical analyzers, the analytes to be characterized are ions and molecules and the feature to be determined is the concentration of said analyte in the biological sample, e.g. a blood or urine sample.

The term 'analyzer' refers to a device being operable to execute one or multiple analyses on biological samples such as blood, urine or saliva samples. An analyzer is operable to load at least one sample into a compartment wherein the analysis is executed, to determine via various chemical, biological, physical, optical or other technical procedures a parameter of the sample or a component of the sample. The sample components, e.g. molecules, ions, proteins and the like are in the following referred to as 'analytes'. The analyzer is operable to measure said parameter and return or store the analysis result in association with a unique identifier of the analyzed sample.

The expression 'analysis result' as used herein encompasses any data that is descriptive of a result of an analysis performed by the analyzer, typically measurement data. The list of possible analysis results returned by the analyzer comprise, but are not limited to, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various type. The analysis result comprises or is associated with the unique identifier of the sample the analysis was performed on.

The phrase "an analysis can be applied" or "a sample is usable for an analysis" and equivalent expressions do not address the question if an analysis can physically be exercised on a particular sample. As long as the sample is not dried out or otherwise severely physically affected by the prolonged storage time, the physical execution of an analysis can be considered as possible in any case. Rather, said and equivalent expressions refer to the question if an analysis performed on a sample will yield a valid result. A valid result is a result which is medically useful, which means that the medical conclusion drawn based on the result is not invalidated by the influence of the sample age on the analysis result. A valid result depends on the physical, biochemical, optical, biological or equivalent parameters of the sample, the reagent and the analysis procedure applied, wherein said parameters may at the moment of analysis not significantly deviate from the parameters of the sample existing right after taking the sample from the patient or laboratory animal. A valid result returned by a biomedical analysis is reproducibly the same for different samples comprising the same concentration and composition of analytes. In case the storage time or conditions have an influence on the analysis result, e.g. because the analyte to be detected is degraded after 2-3 days of storage, the sample should not be used for analysis anymore, because the result of an analysis performed on such a sample would depend on the storage time and condition of the sample which do not correspond to the health status of the patient or other biomedical parameters to be determined in the analysis. The question, if an analysis can or cannot be applied on a sample therefore does not refer to the physical practicability of an analysis but rather refers to the question if the results retrieved by an analysis of a sample is still valid and medically useful given the properties of a particular sample, e.g. the sample age.

The analysis system in accordance with embodiments of the invention further comprises a set of program instructions for assigning 'meta information' to each sample.

The term 'meta information' refers to any kind of information characterizing a feature of the sample or the organism the sample was derived from being of relevance in the context of diagnostics and biomedical analytics. The meta information comprises at least a point in time information, e.g. the time and date the biological sample was taken from the patient or the time the sample was loaded into the analysis system. The meta information may in addition comprise case related data. Case related data is data of the patient from whom the sample was derived, e.g. the health status, diagnoses and medical history of the patient, the name of the patient or the sampling conditions. The meta information may in addition comprise parameters which may be of relevance for sample storage and analysis and in the biomedical context of sample preparation and processing, e.g. on the sample type, the sample quantity, the vessel or tube type the sample is contained in, information on whether the sample is capped or decapped and the like. The content of the meta information may depend on country specific legal regulations ensuring security of patient data. According to an embodiment of the invention, the meta information is stored after sampling to a storage medium, e.g. a relational database. The meta information is stored in association with the unique sample identifier, e.g. a bar code, RFID tag, or a combination of patient ID and sample ID. The term 'stored in association' denotes that the information is stored in a way ensuring that the meta data corresponding to a particular sample can be retrieved given only the unique identifier or other unique features of the sample.

The meta information of a sample can, according to a further embodiment of the invention, in addition comprise storage information, such as the temperature or the humidity within a sample storage unit wherein a sample was stored since the time of sampling. The storage conditions have an important impact on the question if a particular analysis on a sample will return valid result, because an interruption of the cold chain or otherwise unsuitable storage condition may render a sample as unemployable for a particular analysis long before the normal storage period for that sample would end.

According to a further embodiment of the invention, the analysis system comprises a preprocessing unit for preprocessing the samples. The preprocessing comprises tasks such as aliquoting samples, decapping and capping samples. The information, if a particular sample is currently capped or decapped, is added to the meta information of the sample and stored to a storage medium.

The analysis system in accordance with embodiments of the invention further comprises a data storage component, e.g. a database, for storing sets of conditions that have to be met by a sample to be usable for performing the analysis by the analyzer. The data storage component, depending on the embodiment of the invention, can be an integral part of the analysis system or be hosted on an external, separate computer (e.g. a PC or a specialized database server). The content of the data storage component being integral part of the analysis system is, according to embodiments of the invention, integrated into an analysis system specific software program being installed on the same or a further data storage being integral part of the analysis system. According to further embodiments of the invention, the data stored to the integrated or external data storage components is integrated into the middleware of the laboratory or hospital operating the analysis system. According to further embodiments of the invention, the data stored to the integrated or external data storage components is integrated into the LIS of said laboratory or hospital. The integration into a LIS is particularly advantageous, because a LIS is able to integrate said data storage in combination with other analytical or IT services of a laboratory or a hospital and make the data stored in the data storage in combination with said services available for a multitude of different users, e.g. to doctors requesting an analysis to determine the status of health of a patient, medical researchers or the laboratory personnel.

A sample being 'usable for performing the analysis' is a sample which has been stored for a particular time and under particular storage condition guaranteeing that the result obtained by executing a particular analysis on the sample are valid. Each of the condition sets comprises at least a condition on the point in time information of the meta data of the sample. According to one embodiment of the invention, the point in time information is the time and date of sampling. According to a further embodiment of the invention, the point in time information is the time and date of loading the sample into the analysis system or the storage unit or equivalent points of time being of relevance in the context of sample preparation and processing. As will be explained later on in the detailed description section, multiple embodiments of the analysis system according to the present invention exist, some comprising all relevant system components within one single device while other embodiments comprise multiple separate devices.

According to further embodiments of the invention, the analysis system comprises a sample loading unit. The loading and unloading of samples from and to the analysis system is executed automatically by said sample loading unit.

The 'decision unit' is hardware (e.g., a controller, microprocessor, etc.) and/or software, such as a software program which causes hardware to perform the associated functions, such as determine whether results obtained from performing a particular analysis on a sample will return a valid, i.e. medical useful, result. The function(s) of the decision unit is initiated e.g. by receiving an analysis request, which is a request for the execution of a particular analysis on a particular biological sample. To determine, whether the analysis result obtained from that sample will be valid, the decision unit retrieves the meta information assigned to the requested sample and applies conditions on the meta information of the requested sample. The meta information of a sample may comprise the storage time and conditions of a sample or case related data. The applied conditions are taken from a condition set stored in association with a data object representing the requested analysis.

A data object representing a particular analysis will in the following be referred to as 'analytical test'. Said data object can be stored in a volatile and/or non-volatile memory and can be processed by a processing device such as a PC. In case the conditions of the condition set are met by the meta information of the sample, the decision unit returns the decision that the requested analysis can be executed on the requested sample and will return a valid result. Depending on the embodiment of the invention, the decision unit comprises computer-interpretable instructions for executing said decision operation and can be implemented as a modular piece of software or as an integral part of other software programs, e.g. as a part of a program for managing the analysis system. The decision unit can also be implemented as a part of program modules of the middleware or LIS of a laboratory. Said modular or integrated piece of software can be installed on a computer readable storage medium being integral part of the analysis system. According to further embodiments, the decision unit is installed on a PC or server residing outside of the analysis system and being part of the IT infrastructure of the laboratory or hospital. The function of the decision unit can be integrated into a software program for managing the analysis system being installed on an analysis-system internal data storage. According to further embodiments of the invention, the function of the analysis system can in addition or alternatively be integrated into the middleware or LIS of the hospital or laboratory running the analysis system. Independent of the question where the decision unit is installed and if it is implemented as unique piece of software or as a part of other software programs, the decision unit can functionally be integrated into higher-order software systems, as the LIS or the middleware of the instance running the analysis system Depending on the embodiment of the invention, a point in time information used for calculating the age of a sample can be derived at the moment of sampling (e.g. by the lab personnel manually) or automatically at the moment of loading the sample into the analysis system and/or at the moment of loading the sample to a storage unit comprised by the analysis system. Provided that said moments in time are only a few minutes apart from each other, they all can be used to determine the age of the sample. The point in time information of the sample meta information therefore represents any moment in time being indicative of the age of the sample.

A condition for the point in time information could be the condition that the sample should be considered as 'unusable for performing a particular analysis', if the point in time information of the sample's meta information is more than 30 days in the past given a current point in time. The current point in time is the moment in which the decision unit determines if said condition is fulfilled for a particular sample or not.

According to one embodiment of the invention, the analysis system comprises one or multiple condition sets, each condition set corresponding to a particular analysis. Each condition set is stored in association with an analytical test which is a computer-interpretable data object representing a particular type of analysis. Each condition set comprises at least a condition on the maximum age of a sample. The point in time information in the meat information of each sample is used by the decision unit to calculate the age of a sample. If an analysis request requests the execution of a particular analysis on a particular sample, the decision unit retrieves the condition set corresponding to the requested analysis, retrieves the meta information of the sample indicated in the request and calculates the age of the sample by comparing the point in time information of the meta information of the sample with the current time. Each type of analysis supported by the analysis system corresponds to one analytical test which is stored in association with a set of conditions that have to be met by a sample to guarantee that the analysis corresponding to the analytical test data object will return a valid result. The decision unit compares the maximum sample age for a particular analysis as indicated in the condition on the sample age in the condition set corresponding to the analysis with the calculated age of the sample. In case the sample is older than allowed by the condition, the decision unit decides that the sample cannot be used for the requested analysis any more. In case the sample age does not exceed the maximum sample age, the decision unit decides that the execution of the analysis on the sample will return a valid result and will initiate the analysis. The purpose of the conditions on the point in time information is to ensure that an analysis is executed on a sample only in case a valid result for a particular kind of analysis can be expected given the age of a sample.

The impact of the sample age on the applicability of an analysis of a particular kind shall be described by two analyses determining the level of two independent cardiac markers. Both analyses are commonly executed in clinical diagnostics. The analyses determine the NT-proBNP and the Troponin T concentration in human serum samples. NT-proBNP is a marker of cardio respiratory fitness and is used for example for the diagnosis of patients with obstructive sleep apnea or heart insufficiency. Troponin T is a further cardiac marker fur myocardial injury being also indicative of mortality in renal transplant recipients. The serum used for both kinds of analysis has to be stored at a temperature ranging between 2 and 8° C. The maximum storage time of a serum sample still guaranteeing valid results after the execution of an analysis is one day in the case of a Troponin T level analysis and six days for an analysis determining the serum level of NT-proBNP.

Accordingly, a first condition set corresponding to the NT-proBNP analysis comprises a condition on the sample type demanding the sample to be of type 'serum' and a condition on the sample age demanding the sample age not exceeding six days. A data object representing an analysis determining the NT-proBNTP level in serum is stored in a database with an analysis identifier 677 according to one embodiment of the invention. The age of the sample is determined by the point in time parameter in combination with the moment in time the decision unit renders a decision. Depending on the embodiment of the invention, the point in time information may be the date and time of sampling, the date and time of loading the sample into the analysis system or into the storage unit. The point in time information may be any moment in time being indicative of the sample age.

A second condition set corresponding to the Troponin T analysis comprises a condition on the sample type being 'serum', and the sample age not exceeding one day. According to said embodiment, an analytical test (a data object) corresponding to the analysis determining the Troponin T level in serum samples is stored to the database associated to the identifier 58.

A third condition set corresponding to a third type of analysis determines the Troponin T level in urine samples provided the urine sample is not older than 12 days. An analytical test corresponding to said analysis is stored to said database in association with the identifier 899.

The three condition sets corresponding to said three analyses would comprise:

| | |
|---|---|
| Condition set 1 (NT-proBNP) | valid result, if sample = serum and analytical test = 677 and sample age <=6 days |
| Condition set 2 (Troponin T) | valid result, if sample = serum and analytical test = 58 and sample age <=1 day |
| Condition set 3 | valid result, if sample = urine and analytical test = 899 and sample age <=12 days |

The information on the sample type is stored according to one embodiment of the invention in the meta information of a sample. The knowledge on the maximum storage duration of a sample for a particular analysis is stored according to said embodiment in the condition sets. According to other embodiments, the conditions may be implemented more generically and the association of a particular analysis with the maximum storage time of a sample for said analysis may be stored in a separate database table or a separate data structure.

It may also be the case that multiple different chemical analyses are supported by the analyzer which characterize the same analyte or sample property of an analyte with different reactants or different analysis methods. For some analytes, multiple test procedures are available differing, for example, regarding the costs of the procedure and the used reagents, regarding the duration of the analytical procedure or regarding the quality of the retrieved results (quality of quantitative and qualitative measurements: false positive and false negative rates of diagnostic tests). According to a further embodiment of the invention, a cheap and less reliable test is applied at first on all samples and the expensive analysis is repeated solely for samples with a positive first analysis result. In case two different analyses are supported by the analyzer to characterize a particular analyte in a blood sample, analytical test 44 representing an analysis being cheap but being hampered by a high false positive rate, and analytical test 342 representing an analysis being expensive but highly reliable, the structure of the condition sets does not deviate from the condition sets listed beforehand:

| | |
|---|---|
| Condition set 4 | valid result, if sample = blood and analytical test = 44 and sample age <=3 days |
| Condition set 5 | valid result, if sample = blood and analytical test = 342 and sample age <=5 days |

The storage component for storing the condition set can be implemented, according to some embodiments of the invention, as a relational database, wherein the condition sets are stored in tables. The use of relational databases has the advantage that the condition sets can be supplemented by additional condition sets easily and a modification of existing condition sets is also possible without a recompilation of software or the exchange of hardware components. According to other embodiments of the invention, the conditions are comprised by non-relational databases or are hard coded in a software module or in a piece of firmware. According to further embodiments of the invention, the analytical system in addition provides the user with a graphical user interface to modify and supplement the list of condition sets in said data storage component.

According to further embodiments of the invention, the condition sets also comprise conditions on the medical history of a patient being of relevance for a particular test. For example, a diagnostic test to verify a suspected borrelia infection based on PCR is very sensitive and cannot discriminate between a current borrelia infection and infections which have been cured many years ago. If it is known from the medical history of a patient that the patient had a borrelia infection once in his life, this kind of analysis is obsolete as it cannot discriminate the remnants of the past infection from a potentially existing acute infection. The condition sets of embodiments considering in addition case related data in addition comprise conditions on the medical history of a patient. If the analysis 'borreliosis PCR' is represented by the analytical test having the ID 87 and if a verified borrelia infection is encoded in the case data of the sample meta information of a patient (meta_information_code 225), than the corresponding condition set comprises:

| | |
|---|---|
| Condition set 6 | valid result, if sample = blood and analytical test = 87 and sample age <=9 days and meta_information_code <<does not comprise>> 225 |

According to some embodiments of the invention, the analysis system in addition comprises a storage unit for storing biological samples under defined conditions, in the following referred to as storage parameters. Said storage parameters may comprise, but are not limited to, a particular temperature, a particular humidity, a particular luminosity or air composition (indicated e.g. by O2, Nitrogen or CO2 concentration). The storage unit according to further embodiments may in addition comprise inbuilt supplementary storage components such as a shaker or rotor which continuously or with interruptions turn, shake, rotate or otherwise move the biological samples stored therein, e.g. to hold cells or other components of the sample in suspension. The storage unit is, according to further embodiments of the invention, associated with a unit for automatically loading and unloading samples from and to the storage unit. The storage unit comprises technical means, e.g. sensors for light, humidity or temperature, which monitor one or multiple storage parameters. In case the storage unit comprises supplementary storage components for moving or otherwise treating biological samples during the storage time, technical parameters associated with the operation of those technical means may also be monitored and stored as additional storage parameters.

According to further embodiments of the invention, the rotation speed and shaking intervals of said devices are monitored continuously and stored to a data storage in association with the unique identifiers of the samples stored in the storage unit with said parameters. The storage parameters in association with the unique sample identifier therefore reveal the complete storage history of a particular sample, beginning with the point in time in which a sample was loaded into the storage unit. As the monitored storage parameters represent as-is states, in case of a failure, of e.g. the cooling device of the storage unit, this deviation from the to-be state is monitored and can be taken into consideration automatically by the decision unit if the analysis system receives an analysis request for a sample stored under said parameters. In case the failure of the shaker for a prolonged period of time would be detrimental for the validity of the results obtained by a particular analysis, the adding of an additional condition to the condition set stored in association with the analytical test representing said analysis requiring a continuous, uninterrupted shaking process would ensure that samples with fragmentary shaking history are not used for analysis.

The condition sets of some embodiments of the invention comprising in addition a storage unit with sensors for monitoring the storage parameters therefore in addition comprise conditions regarding the storage parameters of a sample. For example, in case a urine sample becomes improper for a particular analysis 16 if the sample is stored for 3 hours or longer at room temperature, storage_condition_67 could be defined as condition, that "a sample has not been stored for 3 hours or longer at room temperature". In case the cooling device fails and the urine sample would have been stored at room temperature for three hours, condition set 7 would reject an analysis request for the execution of analytical test 16 on said sample. Analytical test 16 is a data object representing the requested analysis.

| Condition set 7 | valid result, if sample = urine and sample age <=13 days and analytical test = 16 and storage_condition_67 = true |
|---|---|

Further embodiments of the invention comprise a storage unit for storing biological samples. The storage unit is operable to continuously monitor the storage conditions and store said conditions in association with the unique identifier of the sample stored in the storage unit to a data storage medium. The condition sets comprised by some of said embodiments of the invention comprise in addition conditions on the storage parameters of the biological sample indicated in the analysis request as explained in the example given beforehand. The evaluation of the sample storage condition may involve some additional calculation steps which depend on the type of condition and on the storage parameters affected. According to some embodiments of the invention, the calculation steps are implemented as database queries, e.g. as SQL queries. According to further embodiments of the invention, the calculation steps are hard coded in the software or firmware module controlling the storage unit.

In the following, an exemplary calculation of condition 67 based on the storage parameter 'temperature' shall be given. Condition 67 demands that the storage temperature of said sample must not be higher than room temperature (20° C.) for more than 3 hours during the whole storage life of the sample. According to one embodiment of the invention, the storage unit monitors and stores one temperature value within the storage unit every minute to a storage medium, e.g. a relational database, comprising the monitored storage parameters and a time information, the time information indicating the date and time at which the respective storage parameter was measured and stored. In addition, a timestamp is stored in association with each sample as additional storage parameter whenever the sample is loaded into or unloaded from the storage unit. The timestamp comprises information on the current time and date. At that moment when the decision unit checks whether condition 67 regarding the storage temperature of the sample is fulfilled, the decision unit at first determines those temperature values being monitored during the storage of the indicated sample in the storage unit. Only those temperature values are retrieved which are of relevance for a particular sample. This is achieved by creating SQL queries addressing only those temperature values having associated a time of measurement lying between the moments in time when the sample was loaded to and unloaded from the storage unit. The temperature storage parameters of a sample stored in the storage unit for 2 days comprises according to said embodiment 2×24×60=2880 entries, each entry representing a measured temperature value within the storage unit at a particular point in time. In case an analysis request for said sample is received by the decision unit, the decision unit accesses the storage medium having stored therein all storage parameters of the storage unit. An SQL query executed on the storage parameter database could at first retrieve all temperature entries having been measured within the time window in which the sample had been stored in the storage unit. In the next step, the number of temperature entries is counted whose temperature values exceed or are equal to 20° C. (room temperature). In case the number of detected temperature entries having a temperature value larger than or equal to 20° C. is larger than 180 (3 hours comprise 180 minutes), the condition regarding the temperature storage parameter for a particular analysis is not fulfilled and the corresponding sample is considered as improper for validly performing an analysis on that sample which requires condition 67 to be met by said sample.

The association of storage parameters to the samples stored in the storage unit during measurement of those parameters via a timestamp information for loading and unloading the sample is only one possible embodiment of the invention. The described association of a sample with the storage parameters is beneficial as the storage parameters only have to be stored once and not multiple times for each single sample. However, other embodiments of the invention may deviate from the described implementation schema for various practical reasons. As long as it is ensured that the storage parameters can be assigned to those samples (or their respective unique identifiers) having been stored in the storage unit during the measurement of the storage parameters, other implementation approaches are also possible and meet the spirit and scope of the present invention.

The analysis system according to a further embodiment of the invention comprises a decision unit for determining in response to the receipt of an analysis request for a particular sample whether the requested analysis executed on the indicated sample will yield a valid result. In case the analyzer supports only one kind of analysis, the requested analysis does not necessarily have to be specified within the analysis request explicitly. In case the analyzer supports multiple different kinds of analyses, the requested kind of analysis has to be specified within the analysis request. The decision unit executes the following steps upon receipt of an analysis request:

Determine the sample identifier and, if applicable, the analytical test representing the analysis to be performed according to the analysis request.

Retrieve meta information of the sample given the unique sample identifier. The meta information can be read from the storage medium where the meta information is stored in. The meta information may comprise, in addition to the point in time information, information on the type of the sample.

Calculate the time span between the point in time information contained in the meta information of the sample and the current time and date. This time span represents the age of the sample. According to an embodiment, the point in time information represents the time of sample preparation, of loading the sample to the analysis device or of loading the sample to the storage unit. The calculated time span of the sample according to said embodiments represents the age of the sample measured slightly differently.

Access the storage medium comprising the condition sets.

Evaluate if the storage parameters and the meta information of the sample to be analyzed, e.g. sample age, sample type, storage temperature, medical history of patient, meet the conditions of the condition set corresponding to the requested kind of analysis. In case the corresponding condition set is fulfilled, the result of the evaluation by the decision unit is positive: a valid result can be expected if the requested analysis is executed on the indicated sample.

In case the decision unit returns a positive result, the decision unit submits a command to the controller of the analysis causing the controller to initiate the analyzer. The analyzer in the next step executes the analysis on the sample and returns the results to the controller.

In case the decision unit determines that the requested analysis cannot be performed on the requested sample (a valid result cannot be reliably expected), the decision unit returns a message that the requested analysis cannot be executed. The message comprises the conditions which were not met by the sample.

In case the interval for monitoring the storage condition is not one minute, but two minutes, the computational procedures, e.g. SQL queries, checking the validity of a particular condition have to be adapted accordingly.

According to a further embodiment of the invention, the data storage comprising the condition sets is physically (provided by another hardware component) or logically (provided by another database or data storage structure) distinct from the data storage comprising the meta information and from the data storage comprising the storage parameters of a sample. According to one embodiment of the invention, the storage unit comprises its own database for storing the storage conditions of the samples. Said database is accessible, depending on the embodiment of the invention, via a user interface provided by a LIS or via other hardware or software components of the analysis system and the IT infrastructure used in a laboratory.

According to further embodiments of the invention, the storage parameters of the samples and the meta information could be comprised in one single storage medium. According to a further embodiment, said storage medium could in addition comprise the condition sets. According to some embodiments of the invention, the condition sets, the sample meta information and the storage parameters are stored to relational databases, e.g. an Oracle, MySQL or PostgreSQL database. According to further embodiments of the invention, said data, conditions and algorithms required for the evaluation process in the decision unit is hard coded in the software or firmware of the decision unit.

Various embodiments of the present invention exist, some using as point in time information for calculating the age of a sample the moment at which a sample was loaded into the analysis system. According to other embodiments of the invention, the sampling time or the moment according to which the sample is loaded into the storage unit is used for calculating the age of the sample.

The condition sets used by the decision unit in order to evaluate if a sample can be used for a particular analysis must comprise an appropriate selection of condition sets to ensure that as many information as available for a sample is taken into consideration and checked by the decision unit. The storage parameters monitored by the storage unit may also vary depending on the samples stored therein and on the type of the storage unit. The analyzer according to some embodiments of the invention supports only one type of analysis while other embodiments of the analysis system comprise analyzer supporting multiple different analyses. Due to the multitude and complexity of laboratory workflows, the set of conditions and rules may differ depending e.g. on the type of analyzer and storage unit comprised by the analysis system. In case a storage parameter is available, but not relevant for a particular analysis, the corresponding condition set does not have to comprise a condition for that particular storage parameter or the condition may be defined in a way never to impede a planned analysis. The complexity and content of each condition set depend on the storage parameters provided by the storage unit and on the susceptibility of a particular analyte to be detected on a particular storage condition. For example, the majority of analyses require the sample to be stored at low temperature to prevent a degradation of the biological material by bacteria or other organisms. Some analytes may be degraded upon exposition to daylight, so for analyses detecting the level of those analytes the luminosity of the storage unit is an important parameter.

According to a further embodiment, the storage unit, the analyzer and the pre-processing unit are components of one single block device comprising a transportation line. The transportation line is a line along which samples are transported from one unit of the analysis system to the other, e.g. from the storage unit to the analyzer and back. According to some embodiments of the invention, samples are transported along this transportation line fully automatically. The purpose of this automation in combination with monitoring the storage parameters of the samples, the moment in time when they are loaded and unloaded into or from the analysis system and the storage unit is to completely document all relevant conditions during the whole process chain of the sample. This automation and monitoring ensures that, contrary to the manual handling of samples, the whole process chain is documented for the sample, beginning with the step of loading a sample to the analysis system. The transfer of a sample from the storage unit to the analyzer and back may be executed once or multiple times, depending on the question if a medical professional, e.g. a doctor, decides to repeat a test or to execute additional tests on a sample. Typically, the time span a sample is on its way from one component of the analysis system unit to the next can be measured in minutes while sample storage times range from days to month or even years. The analyzer and storage unit of said embodiment are cooled, while the temperature of the transportation line of the analysis system on which the samples are exchanged between the analysis system components has room temperature. The impact of the conditions of the transportation line analysis system during those few minutes can therefore be considered as negligible compared to the impact of the storage parameters in the storage unit.

According to an embodiment of the invention, one or multiple samples are loaded into the analysis system. The time at which the samples are loaded into the analysis system is stored in association with a unique identifier of the sample to a storage medium. Depending on the analysis to be performed, the samples may be loaded into the pre-processing unit at first where they are capped or decapped, aliquoted or otherwise processed in order to prepare the samples for a particular analysis in the analyzer. A first analysis is then executed on the samples. According to another embodiment of the invention, the analyzer is cooled to a temperature appropriate for the execution of the analysis which at the same time ensures a long storage life of the analyzed samples. After completion of the analysis, the samples are transferred via the transportation line from the analyzer to the storage unit. According to some embodiments of the invention, the samples are loaded into the pre-processing unit on their way from the analyzer back to the storage unit where they are pre-processed (e.g. capped) for storage. The storage unit detects the time point and date (timestamp) at which the samples are loaded into the storage unit and stores said timestamp in association with the unique identifier of the loaded samples. The timestamp can be taken by a software component of the storage device or from a separate device with clock functionality providing the storage device with the date and time information.

It is important to note that according to an embodiment of the invention said transfer steps are executed fully automatically by the analysis system to ensure a complete documentation of the processing pipeline of each sample.

The samples stored to the storage unit can now be requested for one or multiple analysis. If, for example, a doctor decides based on the results of the first analysis that an analysis should be repeated or another additional analysis should be exercised, the doctor may send an analysis request to the analysis system. The request is received by the decision component. The decision unit reads meta information and storage parameters stored in association with the unique sample identifier indicated in the analysis request. In addition, the decision unit reads the condition set corresponding to the requested analysis. The decision unit checks, if all conditions of the condition set corresponding to the requested analysis are met by the parameters specified in the meta information and in the storage parameters of the sample. In case all conditions are met, the decision unit initiates the unloading of the respective sample from the storage unit, the transfer of the sample to the analyzer and the execution of a particular analysis on the sample. After completion of this second analysis, the sample is returned to the storage unit. The timestamp of loading the sample into the storage unit is again recognized and stored in association with the unique identifier of the sample. Optionally, a pre-processing step may have processed the sample before and after analysis, e.g. removed the cap before the analysis and added a cap after the analysis.

A particular advantage of embodiments of the present invention is the possibility provided to the user to determine in advance, if a request for a particular sample and a particular analysis can be expected to yield valid results. The decision unit uses the condition sets, the meta information of a sample, in particular the point in time information indicating the age of the sample and the storage parameters to predict if a requested analysis will return a valid result on a particular sample. In case the system determines that one or more conditions of the condition set associated with a particular analysis are not met by the sample, the analysis is not executed. The decision unit returns a message comprising information on the reasons for not executing the analysis, e.g. because the sample was too old or the storage conditions were inappropriate. The user may then decide to take a new sample, store the sample for other analysis which may still be applicable on the sample, discard the sample or execute the analysis in spite of this message. The sample may still be usable for analyses not related to the diagnosis of the patients status of health, e.g. for testing or training purposes.

The automated decision by the decision unit whether a sample is usable for a particular analysis reduces laboratory work and saves money: the lab personnel does not have to dispose all samples after a predetermined period of time irrespective of the question if a sample can still be used for a particular analysis. The monitoring of storage parameters and the consideration of said parameters by the decision unit is a further beneficial aspect for said objective. The automatic monitoring of storage parameters ensures the detection of any deviation from the designated storage parameters of a sample.

Embodiments of the invention help to reduce costs, because a requested analysis is not performed if the decision unit detects that the requested analysis on a particular sample will not return a valid result given the storage time and conditions of the sample indicated in the analysis request. This information was according to prior art knowledge not considered by the lab personnel or only in so far as the lab personnel disposed samples after a couple of days or few weeks. In case the disposal was not consequently exercised or in case the storage conditions deviated, without the knowledge of the lab personnel, significantly from the optimum storage conditions, an analysis may have been executed on an expired sample. In said case, a wrong analysis result could only be detected after the execution of the analysis in case the results obtained were obviously wrong. In case the results of the analysis were wrong but not obviously wrong, the diagnosis and treatment of a patient based on that erroneous analysis result may also have been wrong.

Embodiments of the present invention help avoiding said sources of error and help reducing time and effort necessary for the handling, management and analysis of biological samples by providing a monitored sampling processing pipeline: a decision logic in the decision unit of the analysis system guarantees the applicability of a requested analysis on a particular sample.

An analysis system according to the present invention has the objective to optimize the workflow of sample handling and analysis and to improve the quality and reliability of analysis results obtained on those biological samples. Embodiments of the invention can be used in the context of biomedical diagnostics in large companies, hospitals and smaller or medium-sized laboratories, but also in the context of pharmacological and biomedical research or forensics. Embodiments of the present invention therefore vary regarding the size of the analysis system, the number and type of analyses supported by the analyzer, the type and number of sample tubes the system is capable to handle and store, the presence of a pre-processing unit and further details which depend on the requirements of the laboratory the analysis system is adapted to.

According to further embodiments of the invention, the operation of the decision unit and the condition sets can be modified in a way to enable an automated evaluation, executed e.g. every hour or every day, which determines the age of biological samples stored in the storage unit. In said evaluation, all samples are disposed which are older than a fixed period of time, e.g. one week or a couple of days depending on the requirements of the laboratory or the analysis to be executed by the analysis system. This embodiment is particularly advantageous for analysis systems performing only one kind of analysis which do not require an advanced evaluation of the age of the sample in relation to a multitude of different analyses and corresponding expiration dates available. Upon execution of each automated evaluation procedure, at least the storage conditions of the samples are checked and deviations from the ideal storage conditions are detected. In case significant deviations are detected, in particular, if an interruption of the cold chain was detected, a warning is returned to the lab personnel that the samples should not be used any more for executing an analysis on them. According to further embodiments, the decision unit initiates the automatic disposal of all samples being older than said predefined period of time or of samples having been stored under storage conditions inappropriate to guarantee a valid analysis result. According to further embodiments, additional conditions, e.g. case-related data, may be checked in addition upon each execution of the automated evaluation process.

Depending on the requirements of the laboratory, the decision logic of the decision unit determining the usability of a sample for a particular analysis given its age, its storage conditions and further parameters can be incorporated in different hardware environments:

According to one embodiment of the invention, the decision unit can be a part of a post-analytical sample storage system. The post-analytical sample storage system is a device for storing various biological samples of different type. According to one embodiment of the analysis system, the post-analytical system comprises a storage unit for 27,000 samples. The storage conditions are monitored and stored automatically to a storage medium contained in the post-analytical system. The post analytical storage unit can be connected to a LIS. The storage parameters and the identifiers of the samples stored to the post-analytical unit can be accessed via the LIS and integrated into the LIS. The system is able to load up to 400 samples per hour into the storage unit.

According to a further embodiment, the post analytical storage unit is connected to the intranet of the laboratory of a hospital and is integrated into the IT infrastructure/middleware of the hospital. The data exchange with the intranet or the LIS is executed via the HL7 Protocol. The post-analytical system can be connected to a separate Roche analyzer. In combination, the post analytical storage unit and the separate Roche analyzer build a complete analysis system for automatically managing and monitoring the workflow of samples. According to a further embodiment of the invention, the exchange of samples between the storage unit and the analysis unit is accomplished manually, i.e. by the lab personnel. Although this embodiment of the invention lacks the benefit of a completely monitored and controlled sample workflow, it still comprises the benefit of monitoring of the storage conditions, of automatically determining the storage time of a sample and of automatically deciding on its usability for a particular kind of analysis. The decision unit decides in case of an analysis request for a particular sample within its storage unit, if the requested analysis will still yield valid results.

According to a further embodiment of the invention, the decision unit is part of an analyzer, the analyzer being linkable to a storage unit. As described beforehand, a fully monitored and automated sample processing pipeline between analyzer and sampler as well as a semi-automated sample handling is possible, depending on the respective embodiment of the invention. The decision unit decides upon any analysis request received by the analyzer if the analysis of a particular sample should be carried out given the storage parameters and storage time of the sample.

According to a further embodiment of the invention, the decision unit is neither part of the analyzer nor of the storage unit, but a separate and independent piece of software stored, for example, on a server connected to the intranet of the hospital or laboratory. The decision unit is a piece of software, here referred to as Work Area Manager (WAM). The decision unit may be an independent software module or be part of the central lab data management system and the middleware of the IT infrastructure of the respective laboratory. According to said embodiment, the decision unit decides for all analysis requests for a particular sample sent via the laboratory middleware system, whether an analysis should be performed or not given the storage time and further storage parameters and meta information of the requested sample.

According to a further embodiment, the decision unit is also a separate and independent piece of software stored, for example, on a server connected to the intranet of the hospital or laboratory. The decision unit software according to said scenario is integrated in the Laboratory Information System LIS of the hospital or laboratory. According to said embodiment, the decision unit decides for all analysis requests for samples managed by the LIS, whether an analysis should be performed or not given the storage time and further storage parameters and meta information of the requested sample Irrespective of the localization oft the decision unit, it has to be ensured that the decision unit has access to the storage media wherein the storage parameters and the meta information associated with the unique identifier of a particular sample have been stored to. The decision unit is also required to have access to the storage medium comprising the condition sets. Depending on the embodiment of the invention, the storage media for the sample meta information, the storage parameters and the condition sets may be separate storage units, e.g. separated databases, located in different hardware modules. According to other embodiments of the invention, in particular those embodiments according to which the decision unit is an integral part of the LIS, all or some of the data repositories may be decoupled from the hardware components of the analysis system (e.g. storage unit or analyzer) and be contained on a separate database server.

In accordance with an embodiment of the invention, a physical network, such as an Ethernet, is utilized for the transmission of analysis requests, analysis results and messages sent by the decision unit. Separate interfaces can be implemented on logical layers of the network transmission protocol for transmission of the various kinds of data. For example, the HL7 interface is used for transmission of a sample identifier and a request to perform a certain analysis on the sample identified by the sample identifier from the data manager application program to the analyzer control computer of the analyzer that is to perform the requested analysis.

By way of illustration, specific exemplary embodiments in which the invention may be practiced are described hereafter with reference made first to FIG. 1.

FIG. 1 shows an embodiment of an analysis system of the invention. The analysis system comprises an analyzer 106 being operable to execute several different analyses on biological samples. The analyzer 106 is controlled by a controller 105, the controller being operable to send commands to the analyzer (indicated in the diagram by an arrow), thereby triggering the initiation of the analysis. The system comprises further a pre-processing unit 104 in which samples are prepared for storage and analysis. According to the depicted embodiment, samples are stored to a storage unit 107 in a capped state. The storage unit comprises one or more sensors 125 for monitoring storage parameters, e.g. a thermometer, and for storing the measured storage parameters 123 in association with a timestamp indicating the moment of measurement in a first data storage component or database 119, in this embodiment, a relational database. The system 102 further comprises a decision unit 109 being operable to read data from a second data storage component or database 120 containing condition sets 124, to read storage parameters for a particular sample from database 119 and to read meta information 126 for a particular sample from a third data storage component or database 118. The analysis system 102 further comprises an interface 122 (e.g., a machine-machine interface, and/or man-machine interface) for receiving an analysis request, the analysis request being indicative of the sample to be analyzed via a unique sample identifier and of the analysis to be executed. In other embodiments of the invention comprising an analyzer being operable to execute only one analysis, the analysis request does not necessarily comprise data being indicative of the kind of analysis to be performed by the analyzer 106.

The system further comprises a database 118 storing therein sample meta information 126. The meta information comprises at least a point in time information 114. The point in time information according to the depicted embodiment indicates the date and the moment in time (a timestamp) at which a sample 100 such as, e.g., a biological sample, was loaded into the analysis system 102 and its label read by the receiver 103. According to other embodiments, the point in time information 114 indicates the moment in time at which a sample was loaded into the storage unit 107 or was taken from the patient. According to said two embodiments, the point in time information may be determined automatically by a component of the storage unit upon loading the sample or may be determined manually by a lab professional upon taking the sample from the patient and adding the time information to the sample's meta information via a GUI provided by the LIS.

According to the depicted embodiment, the unique sample identifier 101 is, e.g., a barcode or RFID chip, etc. being unique for the sample 100 and being indicative of the sample type (blood, urine) and the patient number. The unique sample identifier 101 is read by a further component of the system, a receiver 103 of unique sample identifiers being operable to read the unique sample identifiers 101 of samples loaded into the analysis system 102, such as, e.g., a barcode reader and/or RFID reader. According to the depicted embodiment, a set of program instructions 108 causes a processing component of the analysis system 102 (e.g., the controller/microprocessor which is executing program instructions 108) to receive the current time and date of the moment at which the identifier of the sample is read by receiver 103. The program instructions 108 cause the processing component of the analysis system 102 to assign this time information to the unique sample identifier 101 of the sample 100 and store this information to a database 118. The sample meta information 126 of each sample 100 comprises at least said time information 114, but may in addition comprise further information on the patient and his medical history (case data 116) and information on the sample type 115. It is be appreciated that the processing component (e.g., a controller, microprocessor, etc.) maybe part of an existing entity of the analysis system 102 such as, e.g., the decision unit 109, the analyzer 106, and/or a system/component in communication with the analysis system 102 such as, e.g., a laboratory's or hospital's LIS, middleware, remote computer, etc.

According to further embodiments of the invention, upon loading racks of samples (not shown), the receiver 103 reads the unique sample identifiers 101 as well as unique sample rack identifiers, e.g. rack bar code labels, and uses the position of the sample in the rack for generating a composite unique identifier comprising the rack identifier and a unique sample position. The condition sets 124 stored in database 120 are conditions that have to be met by a sample to be considered by the decision unit 109 as usable for a particular analysis. Each condition set comprises at least a condition on the point in time information 114 of a sample and corresponds to one particular analysis supported by the analyzer 106. Each condition set for a particular analysis may in addition contain conditions on further parameters, e.g. the storage parameters of a sample or on the case data associated to the sample. The sample meta information 126 and the storage parameters having been monitored during the storage of a sample in the storage unit 107 are stored to databases in association with the unique identifier of the sample.

The expression 'in association' denotes, that it is possible e.g. based on the usage of foreign keys in database tables and appropriate SQL queries to assign the meta information and the storage data to a particular sample. The assignation of sample meta information 126 and storage parameters 123 to a particular sample 100 via the unique sample identifier 101 is indicated by two interrupted lines in FIG. 1. The analysis system further comprises an interface 122 for receiving analysis requests. The interface may be a touch screen monitor being an integral part of the analysis system and allowing the lab personnel to specify an analysis request directly via an integral hardware component of the analyzer system. In addition, the analysis system comprises an interface for accessing the system remotely, e.g. via a data manager application program being installed on a computer which is connected to the analysis system via a network, e.g. the intranet of a hospital. The analysis request 112 can be defined on said computer via the data manager application program. The analysis request 112 is then sent via the network and appropriate hardware interface of the analysis system, e.g. an Ethernet card (not shown) to a machine-machine interface of the analysis system 102.

According to further embodiments, the analysis request 112 may be specified in a software component of the laboratory LIS being interoperable with the machine-machine interface of the analysis system 102. To simplify matters and to facilitate the comprehension of figure one, the man-machine interface, e.g. a touch screen monitor, and the machine-machine interface, typically an application programming interface (API), are subsumed as 'interface' 122 for receiving analysis requests. The interface of the depicted embodiment is in addition capable to return a message to the instance submitting the analysis request, e.g. a human entering the request to a touch screen or a computer program on a remote computer of the laboratory's LIS. The message comprises data indicating if the requested analysis could be carried out and, in case of a negative result, why the analysis could not be executed as requested.

In the following, typical sample processing and analysis workflows shall be presented.

The sample 100 is loaded into the analysis system 102. During the loading process, the unique sample identifier 101 of the sample is read by the receiver 103. The set of program instructions 108 causes a processing component of the analysis system 102 to assign a timestamp of the current time to the received unique identifier of the sample. Receiver 103 may in addition have read additional information from the bar code label of the sample, e.g. the type of the sample, or may have read additional information on the patient's medical history from a database comprising patient data (not shown).

The meta information gathered, including the timestamp of loading the sample into the analysis system 102, is stored by the processing component (as instructed by the program instructions 108) to database 118. The meta information is stored in a way ensuring that it can be associated to the unique identifier of the corresponding sample. The sample is in the next step transferred to a pre-processing unit where the sample is decapped for analysis, if necessary. In other embodiments of the invention the pre-processing unit 104 is optional. In such embodiments, the sample is then transferred to the analyzer 106 and a first analysis is carried out. The decision unit 109 may have been queried before the execution of the first analysis whether the analysis will yield a valid result on the sample. As the samples have just recently been loaded into the analysis system 102, the timestamp indicating the sample age will according to this scenario guarantee that the analysis can be executed, provided that the sample has been derived from the patient only a short time before loading the sample into the analysis system. Therefore, the decision unit 109 may not be requested to decide whether the first analysis can be executed or not according to other embodiments of the invention.

After the first analysis has been executed in the analyzer 106, the sample is transferred back to the pre-processing unit 104, where caps are added to the sample for storage. Again, the execution of this capping step is not mandatory in every case and may be missing in other embodiments of the invention.

Finally, the sample is transferred to the storage unit 107 and loaded into the storage unit. Again, a timestamp is taken by a processing component of the analysis system 102 to indicate the moment in time when the sample was loaded into the storage unit 107 and stored in association with the unique sample identifier to database 119. In case the sample is unloaded from the storage unit, again a timestamp is taken by the processing component and stored in association with the sample's identifier as discussed above previously. One or multiple sensors, in the figure subsumed as 'sensors for monitoring storage parameters' 125 continuously (e.g. every minute) monitors storage parameters within the storage unit 107 such as temperature, oxygen concentration or humidity, but also additional technical parameters such as the rotation speed of a shaker. The retrieved storage parameters are stored to a database 119. Each value for a particular temperature is stored in association with the date and time of the moment of measurement of the parameter.

The association of the storage parameters with a timestamp information guarantees in combination with the timestamp information of loading and unloading samples to and from the storage unit 107 that for each sample stored in storage unit 107 the storage parameters relevant for a particular sample can be retrieved. In case a doctor evaluates the results of the first analysis of the patient and comes to the conclusion that the analysis should be repeated or a second, different analysis should be carried out on the sample e.g. in order to verify a first diagnosis, the doctor may submit an analysis request 112 via the interface 122 to the analysis system. As a doctor working with patient typically does not work in the diagnostics department of the hospital, according to said use case scenario the doctor will submit his analysis request from a computer in his office. Said computer is connected via the LIS of the hospital or via the hospital's middleware to the interface 122, such as provided as a machine-machine interface.

According to another use case scenario, a lab-worker decides that a second analysis should be carried out on a particular sample. According to this scenario, the lab worker may enter an analysis request directly via interface 122 such as provided as a man-machine interface, e.g. a touch screen monitor being part of the analysis system, to the analysis system. The analysis request comprises data indicating the sample on which an analysis should be performed, e.g. the unique sample identifier 101 of the sample 100, and data indicative of the type of analysis to be performed. The analysis request is received by the interface 122 and forwarded to the decision unit 109. The decision unit 109 extracts the indicated sample identifier and analysis from the request and reads additional data corresponding to the indicated sample, e.g. meta information 126 from database 118 and storage parameters 123 of the sample from database 119. In addition, decision unit 109 reads a condition set from the condition sets 124 stored in database 120 corresponding to the analysis indicated in the analysis request.

Other embodiments of the invention may comprise an analyzer 106 supporting only one single analysis type. For those analysis systems, the type of analysis does not necessarily have to be indicated in the analysis request as the one single analysis supported by the analyzer is the only analysis method available to the system. After having retrieved all necessary data, the decision unit checks if all conditions are fulfilled. In particular, decision unit 109 checks whether the age of the sample (calculated by the point in time information 114 and the current time of the examining process by the decision unit) still allows the requested analysis executed on the sample to return a valid result. In addition, conditions on storage parameters comprised in the condition set for the requested analysis because they are of relevance for said analysis are checked to ensure that the storage parameters do not significantly deviate e.g. from a required storage temperature optimum or a required oxygen level. It is also checked whether the sample type 115 as indicated in the meta information corresponds to the requested analysis type (an analysis adapted to be executed on blood samples will probably fail when executed on urine samples). In case the condition set for the requested analysis comprises also conditions on case data, e.g. on the medical history of a patient, on the age of a patient or the like, those conditions are also checked by the decision unit 109. In case all checked conditions are fulfilled, the decision unit initiates the unloading of the requested sample from the storage unit, its transfer to the pre-processing unit for decapping and its transfer to the analyzer 106.

The decision unit sends a command to the controller initiating the requested analysis on the requested sample. After the completion of the analysis, the sample is transferred back into the storage unit 107 where again a timestamp is taken upon loading the sample to the storage unit. In case one or multiple conditions are not met by the sample, the decision unit returns a message via interface 122 indicating the conditions which were not fulfilled by the sample.

In case the sample was considered by the decision unit as improper for the execution of the requested analysis, the user may still have the option to initiate the requested analysis despite the negative result returned by the decision unit. For testing or training purposes, for example, such samples may still be usable although the result returned on such kind of sample cannot be used as basis for a diagnosis or other decision of crucial relevance for the health of a patient.

Figure 2:
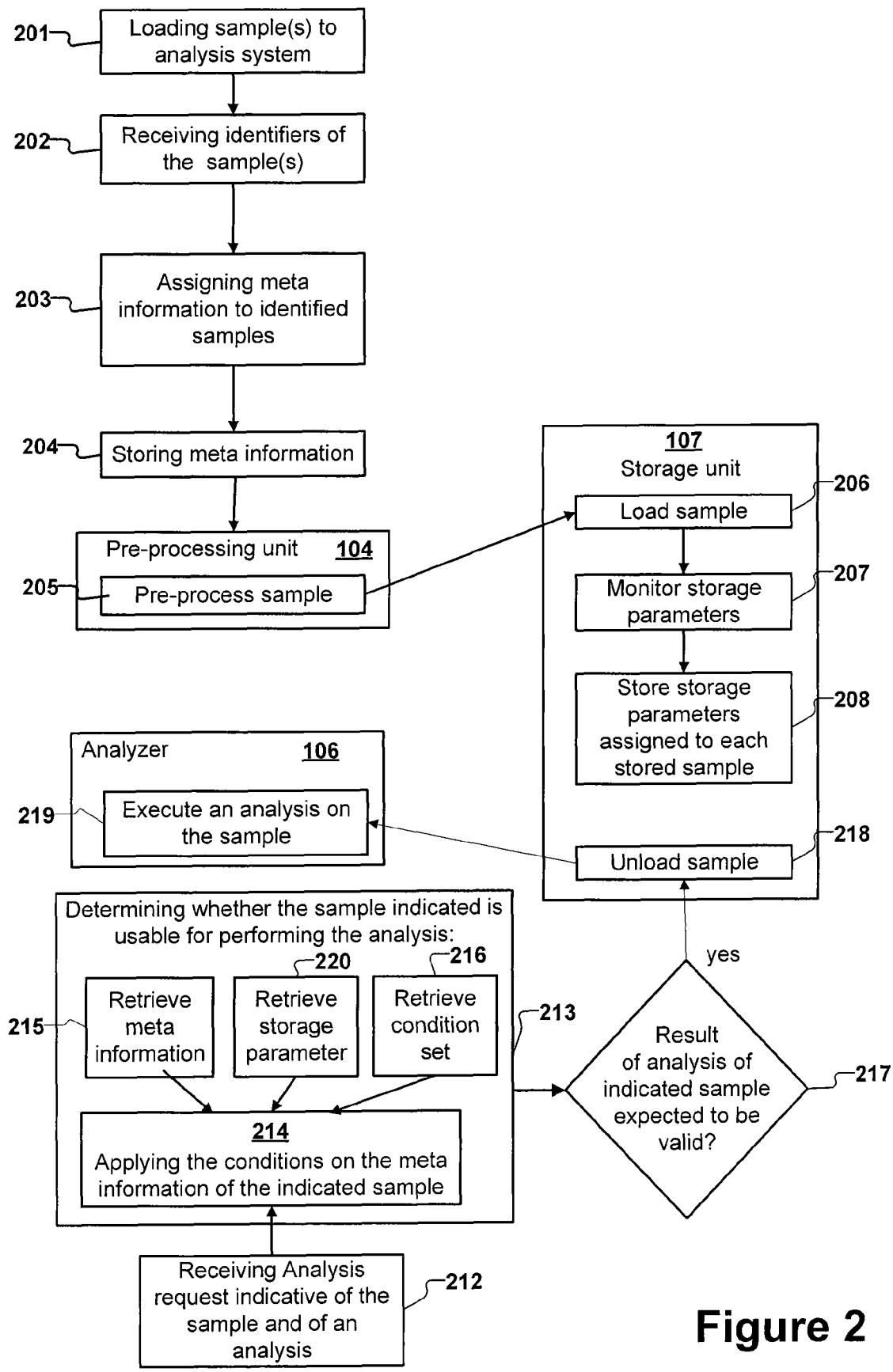
FIG. 2 is a flowchart illustrating an embodiment of a method of the invention.

FIG. 2 describes another possible sample processing and analysis workflow according to a further embodiment of the invention. The workflow depicted in FIG. 2 will be described with reference to the analysis system components as depicted in FIG. 1. In step 201, a sample 100 is loaded into the analysis system 102. In fact, multiple samples may be loaded, e.g. in the form of sample racks, but the workflow is not affected by that aspect. In the next step 202, a unique identifier of the sample is received, e.g. by a bar code reader or a RFID chip reader reading a bar code label or an RFID chip, respectively, attached to the sample.

Depending on the embodiment of the invention, the unique identifier may be composed of the bar code being unique for a rack or for a particular patient not being unique for a sample and additional information, e.g. the position of the sample within the rack. In step 203, meta information is assigned to the sample and stored to a data storage in step 204. In particular, the meta information comprises a point in time information indicating the moment of loading the sample into the analysis system. The meta information 126 may also comprise information on the sample type and case data. The sample loaded into the analysis system is, according to the depicted embodiment, pre-processed in step 205 in a pre-processing unit 104. The pre-processing unit and step 205 may be absent in other embodiments of the invention.

According to the embodiment of the invention described in FIG. 2, the samples are not immediately used for a first analysis but transferred to the storage unit 107. In step 206, the samples are loaded into the storage unit. This step may according to some embodiments of the invention comprise taking a timestamp of the moment of loading the sample into the storage unit to be able to assign the storage parameters to a sample later on. One or multiple storage parameters, e.g. the temperature within the storage unit, is monitored (step 207) continuously, e.g. by measuring the storage parameters every minute. The retrieved storage parameters are stored in step 208 to a data storage. According to some embodiments of the invention, the storage parameters are associated with timestamp information indicating the moment of measuring the respective parameter.

The association of a particular sample to the storage parameters monitored during its storage time may be based according to other embodiments not on a timestamp information, but, for example, solely on the sample identifier. The association of a timestamp information with each storage parameter and the determination and storage of a timestamp for loading and unloading a sample to and from the storage unit is therefore a technically advantageous solution to assign a storage parameters to a sample. Said solution is, however, not the only possible implementation. Other embodiments of the invention may assign each storage parameter measurement value a particular identifier, this identifier being stored in association with the identifier of the biological sample.

In case an analysis request is received by the interface 122 in step 212 indicating a particular sample 100, the request is forwarded to the decision unit 109 which determines in step 213 whether the sample indicated in the request is usable for performing the requested analysis (the analysis on said sample is required to return valid results). Step 213 comprises the steps of retrieving sample meta information (step 215), retrieving storage parameters having been monitored by the storage unit during the storage time of the requested sample (step 220) and retrieving the condition set corresponding to the requested analysis (step 216). The decision unit checks, whether the data associated with the sample, in particular the age of the sample as indicated by the point in time information of the meta information 126, meet the requirements of the condition set of the requested analysis, in particular the requirement that the sample age must not exceed a maximum sample age for a particular analysis. In case the decision unit decides (decision 217) that the results of the requested analysis executed on the requested sample can be expected to be valid, the decision unit initiates the unloading of the requested sample from the storage unit in step 218 and the execution of the requested analysis in the analyzer. In case the decision 217 is negative, a message is returned to the interface 122 indicating the conditions which were not fulfilled by the sample.

Figure 3:
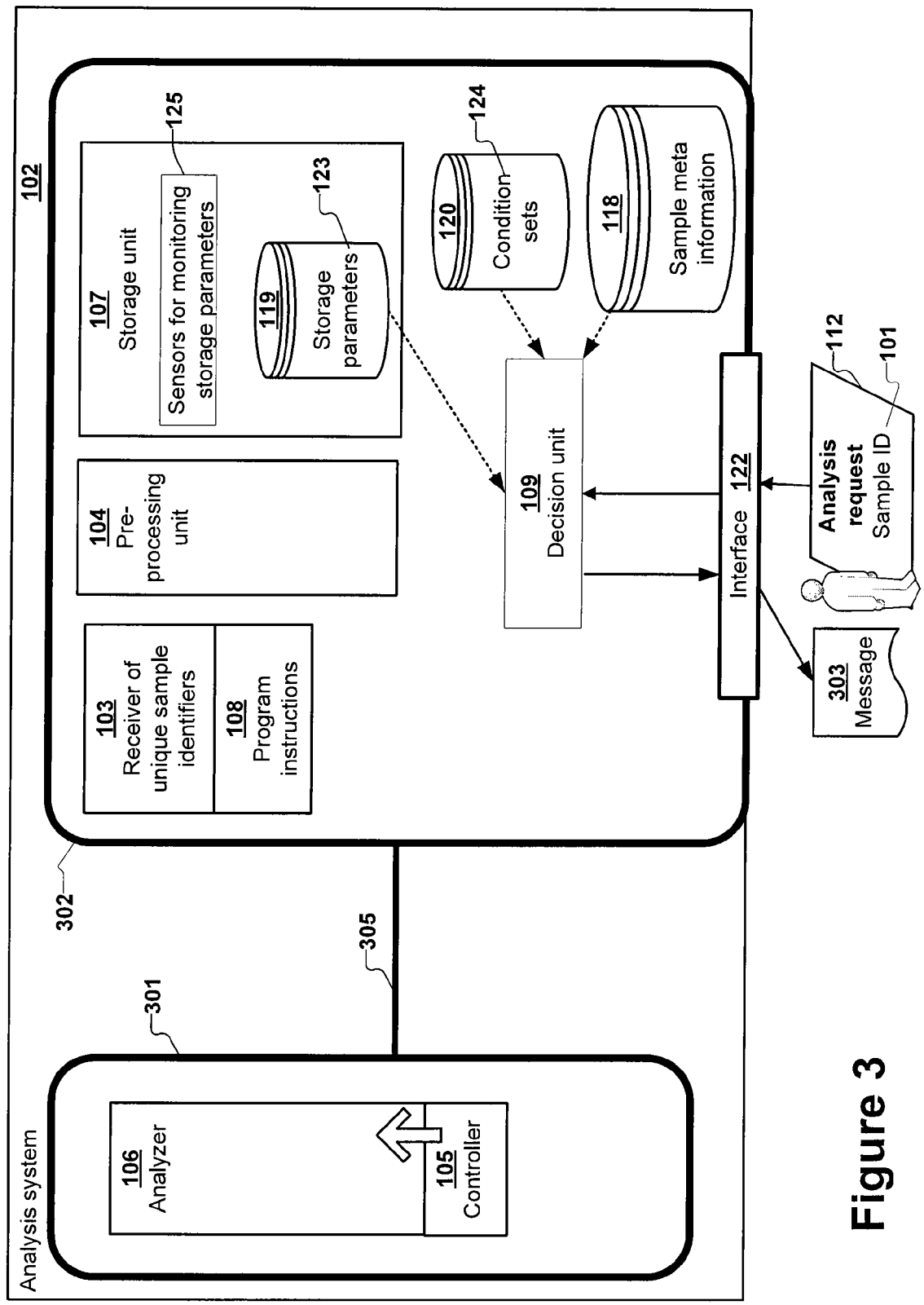
FIG. 3 is a block diagram of a further embodiment of an analysis system of the invention.

FIG. 3 depicts an analysis system according to a further embodiment of the invention. The analysis system consists of two separate devices. The first device 301 is an analyzer comprising a controller 105. The second device 302 is a post-analytical unit comprising a receiver component 103 for receiving unique sample identifiers and program instructions 108 for associating meta information to this identifier. The meta information comprises a point in time information, e.g. a timestamp information indicating the moment of loading the sample into the post-analytical unit 302. The program instructions 108 are in addition operable to cause a processing component (e.g., a controller/microprocessor) of the analysis system 102 to store the unique sample identifier in association with the sample meta information to database 118. The post-analytical unit 302 further comprises a pre-processing unit 104 and a storage unit 107. The storage parameters within this storage unit are continuously measured and stored to database 119 such as, e.g., provided by storage unit 107. In addition, the post-analytical unit 302 comprises a multitude of condition sets 124 in database 120. Each condition set corresponds to a particular analysis and comprises conditions that have to be fulfilled by a particular sample to guarantee that the result of the respective analysis carried out on the sample is valid. Each condition comprises at least a condition on the point in time information being indicative of the age of the sample. The black line 305 depicts a part of the sample transfer line connecting devices 301 and 302 which in combination build a complete analysis system 102. Depending on the embodiment of the invention, the devices 301 and 302 may be linkable in such a way that the transfer of samples from the post-analytical unit 302 into the analyzer device 301 and back is executed fully automatically. In case the decision unit returns a positive result that the analysis can be performed on the requested sample, the sample is unloaded from the storage unit and transferred along the transfer line 305 and back fully automatically.

According to other embodiments of the invention, both devices cannot be fully coupled, e.g. because they were bought from different suppliers. For those embodiments, a human person may be required to read the positive message displayed in interface 122, such as provided as a man-machine interface, e.g. a touch screen monitor, on the post-analytical unit 302, transfer the requested sample to the analyzer unit 301, and transfer the sample back to the post-analytical analyzer and its storage unit 107 after completion of the analysis.

Figure 4A:
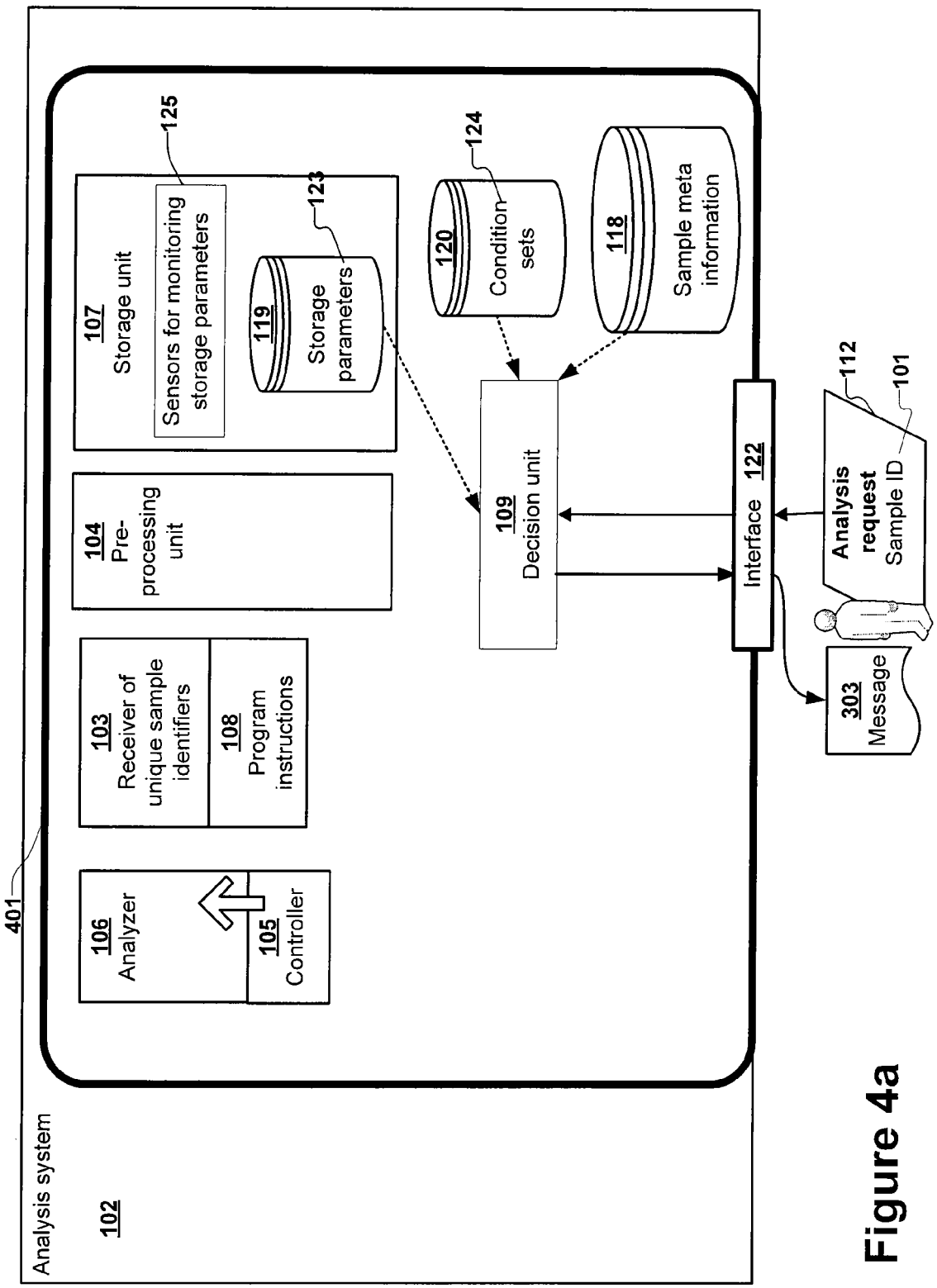
FIG. 4a is a block diagram of a further embodiment of an analysis system of the invention.

FIG. 4a depicts a further embodiment of the invention according to which all relevant system components of the analysis system 102 are comprised within one single device 401. The thick line in FIGS. 3 and 4 does not depict an additional element but merely illustrates that the components of the analysis system may be comprised in one single device or in different devices. According to the embodiment depicted in FIG. 4a, the whole process chain and the handling of the sample is executed fully automatically without requiring a human person to transfer the samples from one system component to the next.

Figure 4B:
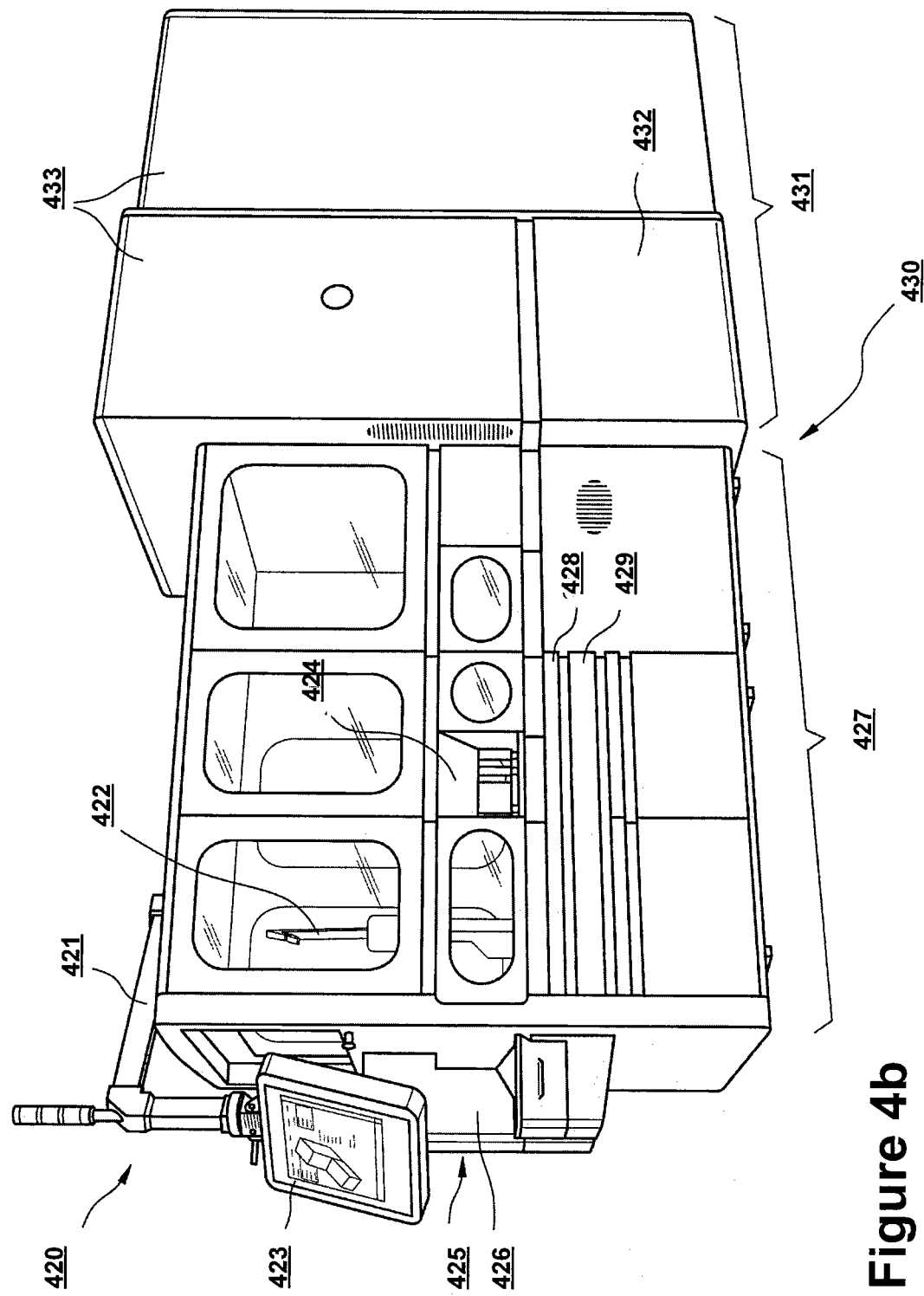
FIG. 4b is a drawing of a further embodiment of an analysis system of the invention.

FIG. 4b shows the analysis system described in FIG. 4a from outside in the form of a realistic drawing. The man-machine interface 420 is embodied as touch screen monitor 423 being coupled to the analysis system via an articulated arm 421. 431 is the storage unit corresponding to the storage unit 107 of FIG. 4a and comprising a refrigerator 433.

The rack handler section 427 has a housing consisting of several outer walls with windows so that operating personnel can have a direct visual overview of the rack handler's functioning. The rack handler section 427 comprises an opening 424 in one of the outer walls through which primary racks can be inserted into the storage retrieval module 430. The opening 424 leads to a primary rack handler area which comprises at least one robotic arm 422 (which can be seen in the depiction of FIG. 4b through one of the windows). Samples can be automatically loaded and unloaded to and from the storage unit via the storage retrieval module 430, which acts as sample loading unit. The rack handler section further comprises drawers 428, 429 through which emptied primary racks can be taken out of the storage retrieval module. Further, the rack handler section comprises a capping station 425 with a feeder tank 426 for tube caps which together constitute the pre-processing unit.

Figure 5:
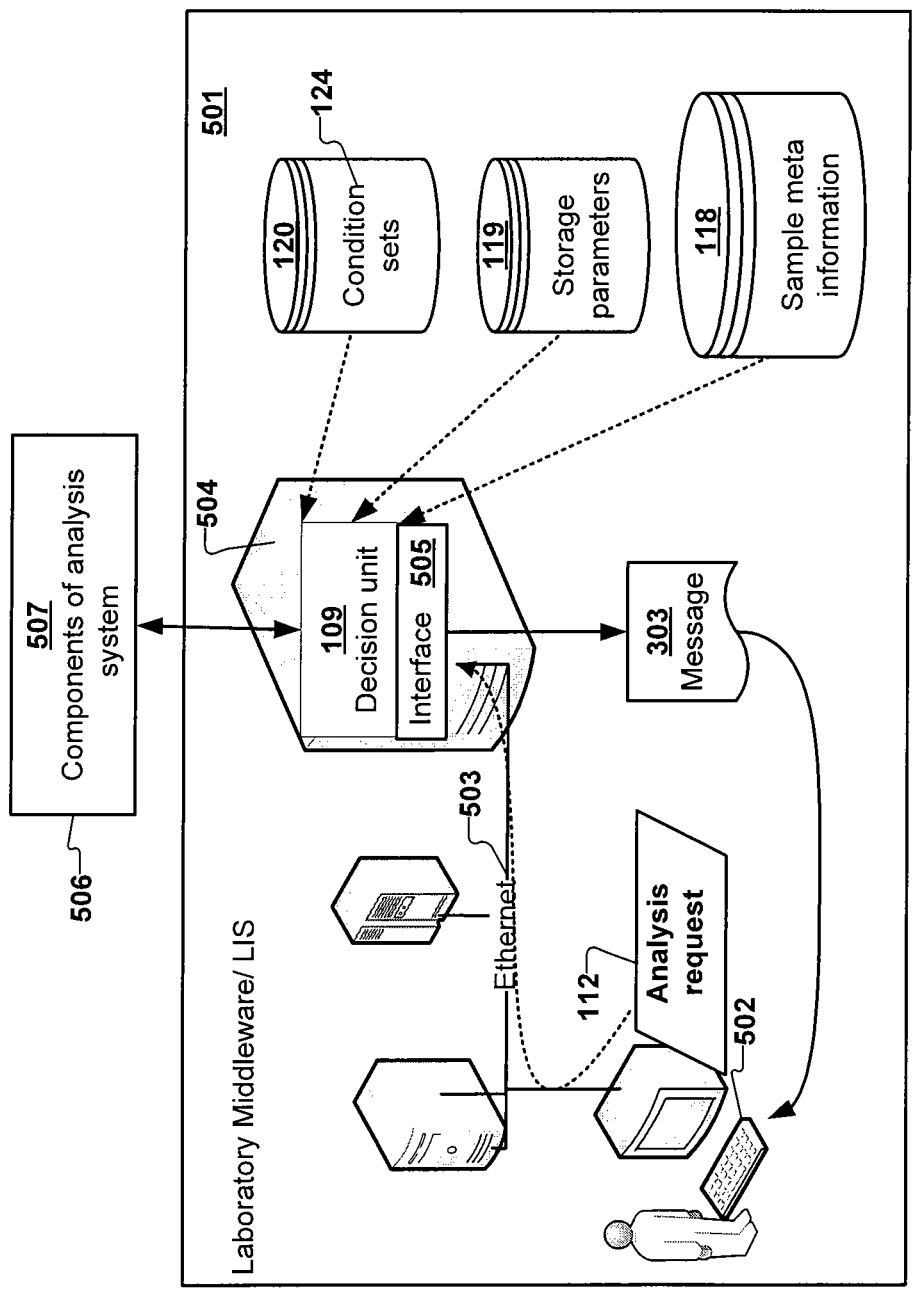
FIG. 5 is a block diagram showing a further embodiment of an analysis system of the invention.

FIG. 5 shows a further embodiment of the present invention which is accessed via a remotely installed software component being part of the IT infrastructure of the hospital, e.g. the middleware or a LIS. Interface 505 is a machine-machine interface and receives an analysis request 303 specified by a user via a network 503. The user uses a data manager application program to specify and submit the request. The data manager program is installed on a computer or terminal 502 and is part of the LIS or of the hospital's IT infrastructure. The decision unit is a piece of software installed on a computer, e.g. a server 504. The exchange of data between the data manager application program and the decision unit 109 is based on the HL7 interface and an XML. The interface 505 can be used for transmitting an analysis request 112 including a sample identifier from the data manager application program that is executed by the remote computer 502 to the decision unit 109 running on computer 504 and for transmitting a message 303 being descriptive of the result of the examination of the decision unit 109 back to the data manager application program. The communication of the decision unit with the components of the analysis system 507 not being depicted as part of the IT infrastructure, e.g. the controller of the analyzer, is referenced by the number 506. The embodiment of the invention as depicted in FIG. 5 comprises the remaining components of the analysis system as depicted in FIG. 1 which are not contained in the LIS system. The databases 118-120 may be located within the devices depicted in FIG. 3 or 4a or may be hosted on separate computers being part of the LIS as depicted in FIG. 6. According to a further embodiment of the invention, the data stored in all databases 118-120 is stored within one single database.

The request that is transmitted using the HL7 interface may be supplemented by additional control data that is transmitted from the data manager application program to decision unit 109 by means of an XML document. Likewise the result data that is transmitted via the HL7 interface can be supplemented by an XML document containing result context data. The communication via the HL7 interface and the exchange of the XML documents may be synchronous or asynchronous.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An analysis system for analyzing biological samples comprising:
   at least one analyzer which performs an analysis, the analyzer operates to characterize a property of an analyte of a biological sample and to acquire at least one measurement value as a result of the characterization;
   a receiver which receives unique sample identifiers, each one of the unique sample identifiers identifying one of the biological samples;
   a set of program instructions which cause assigning meta information to each sample identifier, the meta information comprising at least a point in time information being indicative of the age of the sample, and storing each received identifier and its assigned sample meta information;
   a storage component which stores condition sets, each condition set corresponding to an analytical test and comprising at least one condition that has to be met by a sample to be usable for performing said analytical test by the analyzer, each said condition set comprising at least one condition for the age of the sample;
   an interface which receives an analysis request, the analysis request being at least indicative of one sample to be analyzed and at least one analytical test to be performed;
   a decision unit which operates to determine in response to the receipt of the analysis request whether results to be obtained from performing the analysis on the sample indicated in the analysis request will be valid, wherein this determination is executed by retrieving the meta information assigned to the sample and by applying the at least one condition on the meta information and wherein the at least one applied condition comprises at least a condition on whether the age of the sample allows a valid analysis on the sample, and wherein the decision unit returns the decision that the analysis to be exercised on the indicated sample will return a valid result in case the conditions of the condition set are met by the sample; and
   a controller which operates to initiate the analyzer to perform the analysis using the sample if it is determined that the sample is usable.

2. The analysis system according to claim 1, wherein the point in time information is the time and date of the sampling of the biological sample or the time and date of loading the biological sample to the analysis system.

3. The analysis system according to claim 1,
   wherein the analyzer operates to perform multiple different analyses, wherein each of the multiple analyses differs from all other analyses in at least one aspect, the aspect being selected from the group consisting of the reactant used, the type of the used biological sample, the type of analyte characterized, the analytical procedure applied and the property being characterized;
   wherein the received analysis request is in addition indicative of an analysis to be performed on the sample; and
   wherein the decision unit determines in response to the receipt of the analysis request whether results obtained from performing the analysis indicated in the analysis request on the sample indicated in the analysis request are valid, wherein this determination is executed by retrieving the meta information assigned to the sample, by retrieving the condition set corresponding to the analysis indicated in the analysis request and by applying the at least one condition of the retrieved condition set on the meta information, and wherein the applied at least one condition determines if a valid analysis on the sample can be performed.

4. The analysis system according to claim 1, comprising:
a storage unit which stores biological samples;
at least one sensor which monitors one or more storage parameters within the storage unit;
a set of program instructions which cause assigning the one or more storage parameters to each of the biological samples being stored, the storage parameters being selected from the group consisting of the temperature of the storage unit, the humidity within the storage unit, biochemical, physical and optical properties of the stored sample and technical and physical parameters of the storage unit; and
wherein at least one condition set being associated to an analytical test comprises at least one condition for a storage parameter of the sample indicated in the analysis request, and wherein the decision unit uses a condition for the storage parameter to determine whether the biological sample indicated in the analysis request is usable for performing the analysis.

5. The analysis system according to claim 4, wherein a storage parameter measured within the storage unit is stored in association with an information on the date and time when the parameter was measured, and wherein the analysis system in addition comprises a component which determines the date and time of loading a sample into the storage unit and unloading the sample from the storage unit, wherein the date and time of loading and unloading the sample from the storage unit is stored in association with the unique sample identifier of the sample.

6. The analysis system according to claim 1, comprising a pre-processing unit which pre-processes biological samples for storage and analysis, the pre-processing being selected from the group consisting of capping or de-capping of the sample, creating aliquots of the sample, adding chemical or biological substances, diluting the sample, fractionating the sample and concentrating the sample.

7. The analysis system according to claim 1,
wherein the meta information comprises in addition data on the type of the biological sample, and
wherein at least one condition set comprises at least one condition for the type of the biological sample.

8. The analysis system according to claim 1,
wherein the meta information comprises in addition case related data, the case related data being selected from the group consisting of data for identifying a patient, the disease history of the patient, health related parameters of the patient and data related to the preparation of the biological sample, and
wherein at least one condition set comprises at least one condition for a parameter of the case related data.

9. A computer implemented method for analyzing biological samples by an analysis system, comprising:
receiving unique sample identifiers of the one or multiple biological samples loaded by a receiver of the analysis system;
assigning meta information to each of the one or more biological samples;
storing the meta information assigned to the unique sample identifier of the biological sample;
receiving an analysis request being indicative of the biological sample to be analyzed and of an analytical test to be performed on the biological sample;
determining, by a decision unit of the analysis system and in response to receiving the analysis request, whether the biological sample indicated in the analysis request is usable for performing the analysis by
retrieving from a database the meta information stored in association with the unique sample identifier of the indicated biological sample,
retrieving at least the condition set being associated with the requested analysis from a storage medium, and
checking, if the conditions of the retrieved condition set on the meta information of the indicated biological sample are met, wherein the conditions of the condition set have to be met by a biological sample to be usable for performing the requested analysis on the biological sample; and
executing the requested analysis on the biological sample by an analyzer if according to the results of the previous step the indicated biological sample is usable for the requested analysis,
wherein the meta information comprises at least a point in time information being indicative of the age of the biological sample and wherein the conditions comprise at least a condition on whether the age of the biological sample allows a valid analysis on the biological sample.

10. The computer implemented method according to claim 9, comprising:
sending a command for loading one or multiple biological samples to the analysis system to a sample loading unit of the analysis system; and
automatically loading the sample into the analysis system by the sample loading unit.

11. The computer implemented method according to claim 10, comprising:
loading the one or multiple biological samples to a storage unit;
monitoring storage parameters within the storage unit, the storage parameters being selected from the group consisting of the temperature, humidity, luminosity, air composition, monitored biochemical, physical or optical sample parameters and technical parameters of the storage unit and supplementary storage components;
storing the one or more storage parameters in association with the unique sample identifiers of the one or multiple stored biological samples to a storage medium; and
unloading the indicated biological sample from the storage unit for analysis and for transferring the biological sample to the analyzer if the result returned from the determination of the usability of the biological sample indicated usability of the biological sample for the requested analysis, wherein the condition set for the requested analysis comprises at least one condition on a storage parameter of the biological sample, and wherein the determination whether the biological sample indicated in the analysis request is usable for performing the requested analysis in addition comprises a check if the at least one condition on the storage parameter of the biological sample is met by the biological sample.

12. The computer implemented method according to claim 11, wherein the storage parameters received from the storage unit are stored in association with a particular biological sample by:
determining the time and date when the biological sample is loaded into the storage unit and storing this time information in association with the unique sample identifier of the loaded biological sample,
recording at least one storage parameter in association with an information on time and date of measuring the storage parameter, determining the time and date when the biological sample is unloaded from the storage unit, and storing this time information in association with the unique sample identifier of the unloaded biological sample, assigning recorded storage parameters to the biological sample indicated in the analysis request which are recorded within the time interval defined by the moment of loading the biological sample into the storage unit and unloading the biological sample from the storage unit.

13. The computer implemented method according to claim 10, comprising pre-processing the biological sample after assigning meta information to each of the identified biological samples, the pre-processing being selected from the group consisting of capping or de-capping of the sample, creating aliquots of the sample, adding chemical or biological substances, diluting the sample, fractionating the sample and concentrating the biological sample.

* * * * *